United States Patent
Dhanasekaran et al.

(10) Patent No.: US 7,223,550 B2
(45) Date of Patent: May 29, 2007

(54) BIOSENSOR FOR DEFECTING CHEMICAL AGENTS

(75) Inventors: Natarajan Dhanasekaran, Bryn Mawr, PA (US); John R. Jenkins, Vicarage Hill (GB)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 10/467,223

(22) PCT Filed: Feb. 8, 2002

(86) PCT No.: PCT/US02/03809

§ 371 (c)(1),
(2), (4) Date: Jun. 25, 2004

(87) PCT Pub. No.: WO02/068473

PCT Pub. Date: Sep. 6, 2002

(65) Prior Publication Data

US 2004/0235060 A1  Nov. 25, 2004

Related U.S. Application Data

(60) Provisional application No. 60/267,223, filed on Feb. 8, 2001.

(51) Int. Cl.
  *G01N 33/567* (2006.01)
(52) U.S. Cl. .................................................. 435/7.21
(58) Field of Classification Search ................ 435/7.21
  See application file for complete search history.

(56) References Cited

U.S. PATENT DOCUMENTS

| | | | |
|---|---|---|---|
| 5,128,246 A | 7/1992 | Snyder et al. | 435/69.1 |
| 5,739,029 A | 4/1998 | King et al. | 435/254.21 |
| 5,891,646 A | 4/1999 | Barak et al. | 435/7.2 |
| 5,993,778 A | 11/1999 | Firestein et al. | 424/9.1 |
| 6,004,808 A * | 12/1999 | Negulescu et al. | 435/325 |
| 6,610,511 B1 * | 8/2003 | Carlson et al. | 435/69.1 |
| 2002/0132289 A1 | 9/2002 | Clement et al. | 435/69.1 |

FOREIGN PATENT DOCUMENTS

| | | |
|---|---|---|
| WO | WO 92/17585 | 10/1992 |
| WO | WO 97/35985 | 10/1997 |
| WO | WO 00/35274 | 6/2000 |
| WO | WO 00/43410 | 7/2000 |
| WO | WO 00/50566 | 8/2000 |

OTHER PUBLICATIONS

McClintock, et al., (1997), "Functional Expression Of Olfactory-Adrenergic Receptor Chimeras And Intracellular Retention Of Heterologously Expressed Olfactory Receptors", *Molecular Brain Research*, 48, 270-278.
Offermanns, et al., (1995), "$G\alpha^{15}$ And $G\alpha^{16}$ Couple A Wide Variety Of Receptors to Phospholipase C(*)", *JBC Online*, 270(25), 15175-15180.
Straub, et al., (2001), "Recombinant Maxi-K Channels On Transistor, A Prototype Of Iono-Electronic Interfacing", *Nature Biotechnology*, 19, 121-124.
Restrepo, et al., (1996), "Second Messenger Signaling In Olfactory Transduction", *Journal of Neurobiology*, 30(1), 37-48.
Buck, et al., (1991), "A Novel Multigene Family May Encode Odorant Receptors: A Molecular Basis For Odor Recognition", *Cell*, 65, 175-187.
Mombaerts (1999), "Seven-Transmembrane Proteins As Odorant And Chemosensory Receptors", *Science*, 286, 707-711.
Zhao, et al., (1998), "Functional Expression Of A Mammalian Odorant Receptor", *Science*, 279, 237-242.
Malnic, et al., (1999), "Combinatorial Receptor Codes For Odors", *Cell*, 96, 713-723.
Mori, et al., (1999), "The Olfactory Bulb: Coding And Processing Of Odor Molecule Information", *Science*, 286, 711-715.
Laurent (1999), "A Systems Perspective On Early Olfactory Coding", *Science*, 286, 723-728.
Krautwurst, et al. (1998), "Identification Of Ligands For Olfactory Receptors By Functional Expression Of A Receptor Library", *Cell*, 95, 917-926.
Vidan, et al., (2001), "Making Drug Addicts Out Of Yeast", *Nature Biotechnology*, 19, 1022-1023.
Tucker, et al., (2001), "A Yeast Sensor Of Ligand Binding", *Nature Biotechnology*, 19, 1042-1046.

* cited by examiner

*Primary Examiner*—John D. Ulm
(74) *Attorney, Agent, or Firm*—Drinker Biddle & Reath LLP; Daniel A. Monaco

(57) ABSTRACT

A biosensor for the identification of olfactants, including chemical and biological agents, prefumery, explosives and pharmaceuticals. The biosensors comprise robust eukaryotic cells, such as yeast, into which at least one exogenous olfactory signaling pathway has been genetically integrated to detect molecules of interest.

38 Claims, 6 Drawing Sheets

RI7

Control         Wif-1αRI7

CREBP

Gαolf

Control         Wif-1αRI7

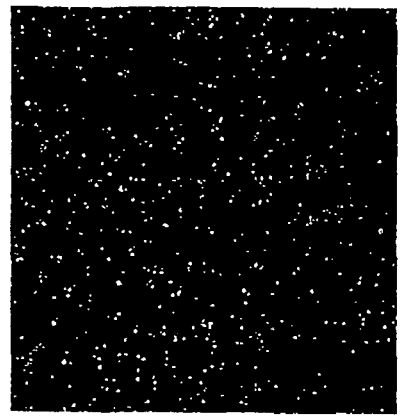
FIG. 6A None
FIG. 6B 6-CHO
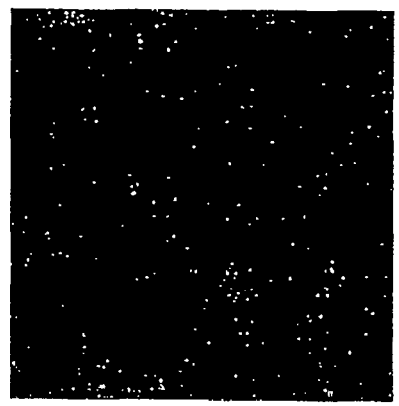
FIG. 6C 7-CHO
FIG. 6D 8-CHO
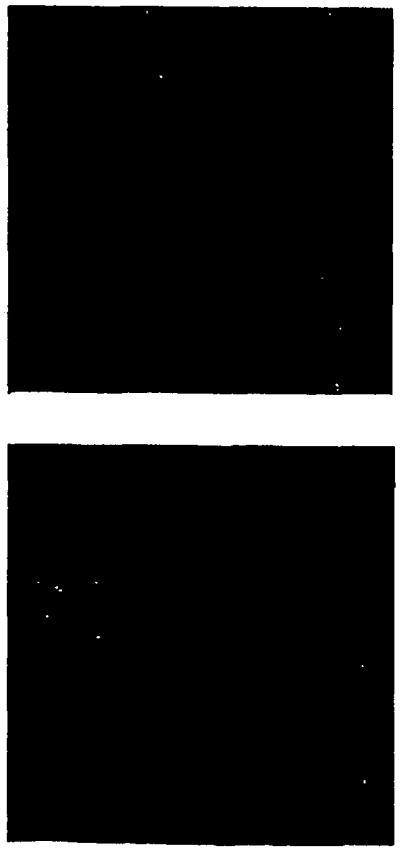

SEQUENCE LISTING

```
<160> NUMBER OF SEQ ID NOS: 35

<210> SEQ ID NO 1
<211> LENGTH: 60
<212> TYPE: PRT
<213> ORGANISM: Schizosaccharomyces pombe

<400> SEQUENCE: 1

Met Arg Gln Pro Trp Trp Lys Asp Phe Thr Ile Pro Asp Ala Ser Ala
 1               5                  10                  15

Ile Ile His Gln Asn Ile Thr Ile Val Ser Ile Val Gly Glu Ile Glu
            20                  25                  30

Val Pro Val Ser Thr Ile Asp Ala Tyr Glu Arg Asp Arg Leu Leu Thr
        35                  40                  45
```

-continued

Gly Met Thr Leu Ser Ala Gln Leu Ala Leu Gly Val
 50                 55                 60

<210> SEQ ID NO 2
<211> LENGTH: 61
<212> TYPE: PRT
<213> ORGANISM: Rattus norvegicus
<220> FEATURE:
<221> NAME/KEY: VARIANT
<222> LOCATION: 35
<223> OTHER INFORMATION: Xaa=any amino acid

<400> SEQUENCE: 2

Met Glu Arg Arg Asn His Ser Gly Arg Val Ser Glu Phe Val Leu Leu
 1               5                  10                  15

Gly Phe Pro Ala Pro Ala Pro Leu Arg Val Leu Leu Phe Phe Leu Ser
             20                  25                  30

Leu Leu Xaa Tyr Val Leu Val Leu Thr Glu Asn Met Leu Ile Ile Ile
         35                  40                  45

Ala Ile Arg Asn His Pro Thr Leu His Lys Pro Met Tyr
 50                  55                  60

<210> SEQ ID NO 3
<211> LENGTH: 35
<212> TYPE: PRT
<213> ORGANISM: Rattus norvegicus

<400> SEQUENCE: 3

Ile Ile Tyr Cys Leu Arg Asn Gln Asp Val Lys Arg Ala Leu Arg Arg
 1               5                  10                  15

Thr Leu His Leu Ala Gln Asp Gln Glu Ala Asn Thr Asn Lys Gly Ser
             20                  25                  30

Lys Ile Gly
         35

<210> SEQ ID NO 4
<211> LENGTH: 32
<212> TYPE: DNA
<213> ORGANISM: Artificial Sequence
<220> FEATURE:
<221> NAME/KEY: variation
<222> LOCATION: 3, 18, 19
<223> OTHER INFORMATION: n = t or c
<220> FEATURE:
<221> NAME/KEY: variation
<222> LOCATION: 9, 12, 15, 21, 24, 27, 30
<223> OTHER INFORMATION: n=inosine
<220> FEATURE:
<221> NAME/KEY: variation
<222> LOCATION: 6, 13
<223> OTHER INFORMATION: n = g or c
<220> FEATURE:
<221> NAME/KEY: variation
<222> LOCATION: 10
<223> OTHER INFORMATION: n = c or a
<221> NAME/KEY: variation
<222> LOCATION: 5
<223> OTHER INFORMATION: n = g or a
<220> FEATURE:
<223> OTHER INFORMATION: Primer

<400> SEQUENCE: 4
aantnnatnn tnntnaannt ngcngtngcn ga                              32

<210> SEQ ID NO 5
<211> LENGTH: 32
<212> TYPE: DNA

<213> ORGANISM: Artificial Sequence
<220> FEATURE:
<223> OTHER INFORMATION: Primer
<220> FEATURE:
<221> NAME/KEY: variation
<222> LOCATION: 12, 15, 21, 24, 27, 30
<223> OTHER INFORMATION: n=inosine
<220> FEATURE:
<221> NAME/KEY: variation
<222> LOCATION: 3, 6, 9, 18, 25
<223> OTHER INFORMATION: n=t or c
<220> FEATURE:
<221> NAME/KEY: variation
<222> LOCATION: 13
<223> OTHER INFORMATION: n=g or a
<220> FEATURE:
<221> NAME/KEY: variation
<222> LOCATION: 10
<223> OTHER INFORMATION: n=c or a

<400> SEQUENCE: 5
aantanttnn tnntnaanct ngcnntngcn ga          32

<210> SEQ ID NO 6
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 3, 4, 9
<223> OTHER INFORMATION: n=t or c
<220> FEATURE:
<221> NAME/KEY: variation
<222> LOCATION: 5, 16
<223> OTHER INFORMATION: n=t or a
<220> FEATURE:
<221> NAME/KEY: variation
<222> LOCATION: 6, 12, 15, 18, 21, 24, 27, 30
<223> OTHER INFORMATION: n=inosine
<220> FEATURE:
<221> NAME/KEY: variation
<222> LOCATION: 26
<223> OTHER INFORMATION: n=g or c
<220> FEATURE:
<221> NAME/KEY: variation
<222> LOCATION: 10
<223> OTHER INFORMATION: n=a or c

<400> SEQUENCE: 6
aannnnttnn tnatnncnct ngcntnngcn ga          32

<210> SEQ ID NO 7
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 3, 6, 9, 21, 30
<223> OTHER INFORMATION: n=inosine
<220> FEATURE:
<221> NAME/KEY: variation
<222> LOCATION: 1
<223> OTHER INFORMATION: n=c or a
<220> FEATURE:
<221> NAME/KEY: variation
<222> LOCATION: 7, 15, 18, 24, 27
<223> OTHER INFORMATION: n=c or t
<220> FEATURE:
<221> NAME/KEY: variation
<222> LOCATION: 22
<223> OTHER INFORMATION: n=a or t

```
<220> FEATURE:
<221> NAME/KEY: variation
<222> LOCATION: 23
<223> OTHER INFORMATION: n=c or g
<220> FEATURE:
<221> NAME/KEY: variation
<222> LOCATION: (27)...(27)
<223> OTHER INFORMATION: n=t or c
<220> FEATURE:
<221> NAME/KEY: variation
<222> LOCATION: (30)...(30)
<223> OTHER INFORMATION: n=inosine

<400> SEQUENCE: 7
ngnttnntna tgtgnaanct nnnnttngcn ga                             32

<210> SEQ ID NO 8
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: 3, 6, 12, 15, 21, 24, 27, 30
<223> OTHER INFORMATION: n=inosine
<220> FEATURE:
<221> NAME/KEY: variation
<222> LOCATION: 9, 18, 19
<223> OTHER INFORMATION: n=t or c
<220> FEATURE:
<221> NAME/KEY: variation
<222> LOCATION: 22
<223> OTHER INFORMATION: n=a or t
<220> FEATURE:
<221> NAME/KEY: variation
<222> LOCATION: 23
<223> OTHER INFORMATION: n=c or g

<400> SEQUENCE: 8
acngtntana tnacncannt nnnnatngcn ga                             32

<210> SEQ ID NO 9
<211> LENGTH: 33
<212> TYPE: DNA
<213> ORGANISM: Artificial Sequence
<220> FEATURE:
<223> OTHER INFORMATION: Reverse Primer
<220> FEATURE:
<221> NAME/KEY: variation
<222> LOCATION: 4, 13, 16, 22, 25, 28
<223> OTHER INFORMATION: n=inosine
<220> FEATURE:
<221> NAME/KEY: variation
<222> LOCATION: 5, 24, 27
<223> OTHER INFORMATION: n=c or t
<220> FEATURE:
<221> NAME/KEY: variation
<222> LOCATION: 6
<223> OTHER INFORMATION: n=g or t
<220> FEATURE:
<221> NAME/KEY: variation
<222> LOCATION: 7, 19, 31
<223> OTHER INFORMATION: n=g or a
<220> FEATURE:
<221> NAME/KEY: variation
<222> LOCATION: 15
<223> OTHER INFORMATION: n=a or t
<220> FEATURE:
<221> NAME/KEY: variation
<222> LOCATION: (17)...(18)
<223> OTHER INFORMATION: n=a or c

<400> SEQUENCE: 9
```
ctgnnnnttc atnannnnnt anannnanngg ntt        33

<210> SEQ ID NO 10
<211> LENGTH: 31
<212> TYPE: DNA
<213> ORGANISM: Artificial Sequence
<220> FEATURE:
<223> OTHER INFORMATION: Reverse Primer
<220> FEATURE:
<221> NAME/KEY: variation
<222> LOCATION: 8, 20, 23, 26
<223> OTHER INFORMATION: n=inosine
<220> FEATURE:
<221> NAME/KEY: variation
<222> LOCATION: 2, 5, 11, 14, 17, 29
<223> OTHER INFORMATION: n=a or g
<220> FEATURE:
<221> NAME/KEY: variation
<222> LOCATION: 1
<223> OTHER INFORMATION: n=g or t
<220> FEATURE:
<221> NAME/KEY: variation
<222> LOCATION: 4
<223> OTHER INFORMATION: n=c or g

<400> SEQUENCE: 10
nntnnttnag ncancantan atnatnggnt t        31

<210> SEQ ID NO 11
<211> LENGTH: 32
<212> TYPE: DNA
<213> ORGANISM: Artificial Sequence
<220> FEATURE:
<223> OTHER INFORMATION: Reverse Primer
<220> FEATURE:
<221> NAME/KEY: variation
<222> LOCATION: 3, 12, 15, 21, 24, 27
<223> OTHER INFORMATION: n=inosine
<220> FEATURE:
<221> NAME/KEY: variation
<222> LOCATION: 6, 9, 18, 30
<223> OTHER INFORMATION: n=g or a

<400> SEQUENCE: 11
tcnatnttna angtngtnta natnatnggn tt        32

<210> SEQ ID NO 12
<211> LENGTH: 32
<212> TYPE: DNA
<213> ORGANISM: Artificial Sequence
<220> FEATURE:
<223> OTHER INFORMATION: Reverse Primer
<220> FEATURE:
<221> NAME/KEY: variation
<222> LOCATION: 6, 12, 15, 21, 27
<223> OTHER INFORMATION: n=inosine
<220> FEATURE:
<221> NAME/KEY: variation
<222> LOCATION: 9, 18, 24, 30
<223> OTHER INFORMATION: n=a or g
<220> FEATURE:
<221> NAME/KEY: variation
<222> LOCATION: 3
<223> OTHER INFORMATION: n=c or t

<400> SEQUENCE: 12
gcnttngtna anatngcnta nagnaanggn tt        32

<210> SEQ ID NO 13
<211> LENGTH: 32
<212> TYPE: DNA
<213> ORGANISM: Artificial Sequence

```
<220> FEATURE:
<223> OTHER INFORMATION: Reverse Primer
<220> FEATURE:
<221> NAME/KEY: variation
<222> LOCATION: 6, 12, 15, 21, 26, 27
<223> OTHER INFORMATION: n=inosine
<220> FEATURE:
<221> NAME/KEY: variation
<222> LOCATION: 3, 9, 18, 30
<223> OTHER INFORMATION: n=a or g
<220> FEATURE:
<221> NAME/KEY: variation
<222> LOCATION: 10, 16, 24
<223> OTHER INFORMATION: n=c or g
<220> FEATURE:
<221> NAME/KEY: variation
<222> LOCATION: 11
<223> OTHER INFORMATION: n=a or t

<400> SEQUENCE: 13
aantcnggnn nncgnnanta natnannggn tt                                32

<210> SEQ ID NO 14
<211> LENGTH: 32
<212> TYPE: DNA
<213> ORGANISM: Artificial Sequence
<220> FEATURE:
<223> OTHER INFORMATION: Reverse Primer
<220> FEATURE:
<221> NAME/KEY: variation
<222> LOCATION: 3, 6, 9, 21, 27
<223> OTHER INFORMATION: n=inosine
<220> FEATURE:
<221> NAME/KEY: variation
<222> LOCATION: 1, 4
<223> OTHER INFORMATION: n=g or c
<220> FEATURE:
<221> NAME/KEY: variation
<222> LOCATION: 2, 5
<223> OTHER INFORMATION: n=a or t
<220> FEATURE:
<221> NAME/KEY: variation
<222> LOCATION: 12, 18, 24, 30
<223> OTHER INFORMATION: n=a or g

<400> SEQUENCE: 14
nnnnnnccna cnaanaanta natnaanggn tt                                32

<210> SEQ ID NO 15
<211> LENGTH: 25
<212> TYPE: DNA
<213> ORGANISM: Artificial Sequence
<220> FEATURE:
<223> OTHER INFORMATION: Reverse primer
<220> FEATURE:
<221> NAME/KEY: variation
<222> LOCATION: 12, 15
<223> OTHER INFORMATION: n=a or g
<220> FEATURE:
<221> NAME/KEY: variation
<222> LOCATION: 13
<223> OTHER INFORMATION: n=c or g
<220> FEATURE:
<221> NAME/KEY: variation
<222> LOCATION: 17
<223> OTHER INFORMATION: n=a, g or t
<220> FEATURE:
<221> NAME/KEY: variation
<222> LOCATION: 20, 22, 23
<223> OTHER INFORMATION: n=a, g or dP-CE phosphoramidite

<400> SEQUENCE: 15
ggggtccgga gnntnanatn anngg                                        25
```

```
<210> SEQ ID NO 16
<211> LENGTH: 30
<212> TYPE: DNA
<213> ORGANISM: Artificial Sequence
<220> FEATURE:
<223> OTHER INFORMATION: Reverse primer
<220> FEATURE:
<221> NAME/KEY: variation
<222> LOCATION: 16, 25
<223> OTHER INFORMATION: n=a, c, g or t
<220> FEATURE:
<221> NAME/KEY: variation
<222> LOCATION: 22, 23, 28, 29
<223> OTHER INFORMATION: n=c or t

<400> SEQUENCE: 16
ggggctgcag acaccnatgt anntnttnnt                              30

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
agccagcagg catggggtgt ttgg                                    24

<210> SEQ ID NO 18
<211> LENGTH: 24
<212> TYPE: DNA
<213> ORGANISM: Artificial Sequence
<220> FEATURE:
<223> OTHER INFORMATION: Reverse primer

<400> SEQUENCE: 18
tcacaagagt tcgtactgct tgag                                    24

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
taggtaccga gctcttacgc gtgctagcgc a                            31

<210> SEQ ID NO 20
<211> LENGTH: 35
<212> TYPE: DNA
<213> ORGANISM: Artificial Sequence
<220> FEATURE:
<223> OTHER INFORMATION: Reverse Primer

<400> SEQUENCE: 20
gctctagatt acttgtacag ctcgtccatg ccgag                        35

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
atggagcgaa ggaaccacag tggg                                    24
```

<210> SEQ ID NO 22
<211> LENGTH: 26
<212> TYPE: DNA
<213> ORGANISM: Artificial Sequence
<220> FEATURE:
<223> OTHER INFORMATION: Reverse Primer

<400> SEQUENCE: 22
ctaaccaatt ttgctgcctt tgttgg                                  26

<210> SEQ ID NO 23
<211> LENGTH: 33
<212> TYPE: DNA
<213> ORGANISM: Artificial Sequence
<220> FEATURE:
<223> OTHER INFORMATION: 5' Dra III Primer

<400> SEQUENCE: 23
agggcgatgg cccactacgt gaaccatcac cct                          33

<210> SEQ ID NO 24
<211> LENGTH: 37
<212> TYPE: DNA
<213> ORGANISM: Artificial Sequence
<220> FEATURE:
<223> OTHER INFORMATION: NT-RX Primer

<400> SEQUENCE: 24
agagagagat ctgcagatac atgggtttgt ggagggt                      37

<210> SEQ ID NO 25
<211> LENGTH: 36
<212> TYPE: DNA
<213> ORGANISM: Artificial Sequence
<220> FEATURE:
<223> OTHER INFORMATION: CT-RX Primer

<400> SEQUENCE: 25
agagagagat ctactagtat ctactgcttg cgcaac                       36

<210> SEQ ID NO 26
<211> LENGTH: 33
<212> TYPE: DNA
<213> ORGANISM: Artificial Sequence
<220> FEATURE:
<223> OTHER INFORMATION: 3'Hind III Primer

<400> SEQUENCE: 26
ctagccgcgg taccaagctt actcgaggtc ttc                          33

<210> SEQ ID NO 27
<211> LENGTH: 3504
<212> TYPE: DNA
<213> ORGANISM: Rattus norvegicus

<400> SEQUENCE: 27
gtctcgctgg ctctggtgcg ccttcctact tgcctgatcg gagtgcgagc cagcaggcat        60
ggggtgtttg ggcaacagca gcaagaccgc ggaagatcag ggcgtggatg aaaaggaacg       120
ccgggaggcc aacaaaaaga tcgagaagca gttgcagaaa gagcgcctgg cttacaaagc       180 gaccccaccgc ctgctgcttc tgggggctgg tgagtccggg aaaagcacta tagtcaaaca       240
gatgaggatc ctacacgtca atggcttcaa ccccgaggaa aagaagcaga aaattctgga       300

```
catcaggaaa aatgtcaaag atgctttagt gacaatcatt tcagcaatga gtaccataat    360
acctccagtt ccactggcca accctgagaa ccagtttcgg tcagattaca tcaagagcat    420
agcccctatc actgactttg aatattccca ggagttcttt gaccacgtga agaagctgtg    480
ggatgatgag ggagtgaagg cctgctttga gagatccaac gagtaccagc tgatcgactg    540
tgcacaatac ttcctggaaa ggattgacag cgtgagtctg gttgactaca cacccacaga    600
ccaggaccta ctcagatgca gagtgctgac atcaggatc tttgagacac gattccaagt    660
ggacaaagtg aactttcaca tgtttgacgt tggaggccag agggatgaga aagaaaatg    720 gatccagtgt tttaacgatg tcactgccat catctatgtg gcagcctgca gcagctacaa    780
catggtgatc cgggaagata acaaccacca cagactccgg gagtcgctgg acctgtttga    840
aagcatctgg aataacaggt ggttacgaac catttccatc atcctgttct tgaacaaaca    900
agatatgctg gcagaaaaag tcttggccgg gaagtcaaaa attgaagact atttcccgga    960
gtatgccaac tatactgtcc ctgaagatgc aacaccagat gcaggagaag atcccaaagt   1020
tacaagagcc aagttcttta tccgggatct gttcttgagg atcagcacag ccacgggtga   1080
tggcaaacat tactgctacc ctcacttcac ctgcgccgtg gacacagaga acatccgcag   1140
agtgttcaac gattgtcgtg acatcatcca gagaatgcac ctcaagcagt acgaactctt   1200
gtgagggcca cccacccacc cctcctcctc ctcactgctg cctttcctcc ctcttgacca   1260
ccccatgagg cagcatatcc ccctagcctg cgtgtctgtc caccccgagc caaggtaggg   1320
agtagtgagt gtctagtgtc atcggactgc cgtctgtcct gtcctaggta tgcctatgtg   1380
tgaccaccaa gcctctggct acctctgttc cccaaggttt ggttctgtga ctttgtttc    1440 actggacaaa acagcctccc accaccaatt tgtatccccg tatcaccctc tgggtggtac   1500
tgcagtggat tttctctggg tgggaatcta tttattcttt gatggaatgg ttgatgggtt   1560
gaatcatcaa agacagcttg gtgaacgggg gaaatacatt gttttcaagt tatcaagcat   1620
gatcacaaaa ctgtccggac agtgccacgc acttggtttt tccctttata aaaggttggg   1680
ctacccagtg tctgcccctt ctggtctgca ttggcccagg gcttaaagca gatccacgtc   1740
agcaacagaa gacgaggacc ttttcagcc acagttgcaa tggctataag ccttgggcat    1800
ttgggttaga gcacttctgg gagccttta cacttgggca gaaagccggc acattcact    1860 actaatggtg tcctgtctat aaacaagggg tcctctacac cttcctgata gctgggcata   1920
gtccttcctg tcttctttct gttgttgctt taccagactg tacagaccac aagatgtact   1980
actcttttct gtggctactc cagaagcctc cttgtagagt tccgtgcctt ggtggcggct   2040
atacctgtaa ggaaacgtgt ccctcctgtg ccaagcagcc tgcagtccac acagcctgct   2100
gcttcacagt ggggaatcag tagtatctgc ccatcttagg atattttat caggttggca   2160 cttatgaag actcggtgat tttagaatca tccactttac cagcagtatc ttcccaacac   2220
tgaaactgtt gcagccaccc gctttttactg ctccaaacct gagctgctgc acacattggg   2280
atgacccgct ttcaaggctt aaattacaat caattctttt ttcagggttc taaggggttc   2340 cccccactc ccctctcaag gtgatctgtt ttcaatgacc ccttcaagtt ctgtagtcag    2400
gagcaggcca accatcccctt agttaagttc tacacacagg ccaccaaaca agaaaccggt   2460
ggtcagagga aagcacaggg gtgtccatgt tgtatatggc tgaggacaat aaggatgatg   2520
tcatctgaag atgaaatata caaaactact tatttattat ctgtctctct atttgctagg   2580
gatgagccca gcaccagtg catgctaggc aagcactcta cagctagtcc atatccccag   2640
ccacaactcc agccctcaca aaaacctttta ttttaaatat aaagacaaaa taaatggctt   2700
```

-continued

```
ctcctcacat gtgtaagatc tgcgaataca acctcaagtt atggtaggac acctagaaaa      2760
cgacacagca catactgtct aagcctgagg ctttgggggt catttctctt aggcttaaag      2820
ttacctgtaa agatgtccca agttaagttt ctaacagtac agataggaag gagtgacagc      2880
ctgcaattct ccttattgtt gctttaagtt tattccgtaa actggcattg tagaactctc      2940
taaaaactca tcctggccga gatgttcttc cgagaaaggg tacagcactt tccccagctc      3000
ctcaccactg tcttctggaa ccattcccta gcattgcata aaacttccct ctgaagccag      3060
gcaatgaggg tgcacacctt taatctcagc gctcggaaaa acagacaggc acatctcagt      3120
gttcgaggcc agcctggtct acagagtgag ttccaggaca actagtgctt cacagagaaa      3180
ccctgtctca aacaaaacaa actaacttct gtctgaacca acacatgaaa tgacagcggc      3240
tttcagttcc ccctgcactc tcaaagcaaa gcaagaagaa aaacttgcac acacacacac      3300
acacacacac acacacacac acacacacgt gtgaggtttt ataccacagt gtgcattact      3360
actctacagt tccctgctga ctgaatgact attgaagagt ttcgttgggg ctgaatgtgt      3420
aactctgacg gagcacatgc tcagcatgcg tgagacctga gatcaatcaa gagaaacgag      3480
atataaataa aatcaaatca ttag                                            3504
```

<210> SEQ ID NO 28
<211> LENGTH: 1731
<212> TYPE: DNA
<213> ORGANISM: Schizosaccharomyces pombe

<400> SEQUENCE: 28

```
tctctgacaa agatgaaaaa taattttttaa gaactgtcta aacaatagta aatccttttg       60 tttttttgttt cgaatctgtt taaactacaa ttttgcaatt gttcgaacag cattccattg      120
gtgtgttttg agtccatata tttggaaatt tgctgtatat cttcaagcga aaatttaact      180
tttgagacat agaagtgttt tctggaaatt ctaaacaaag aggaattatt ggcataacag      240
ttcattggga aactgagtca tcaagtgctt tacaaatcac atttttaaac ttcttaaact      300
aaaaaaatct cgggtttata ttgttcttgc tccctctgac attatgagac aaccatggtg      360
gaaagacttt actattcccg atgcatccgc aattattcac caaaatatta ccattgtctc      420
tattgtagga gagattgaag tgccagtttc aacaattgat gcatatgaaa gagatagact      480
tttaactgga atgactttgt ctgcccaact tgctttagga gtccttacca ttttgatggt      540
ttgtctattg tcatcatccg aaaaacgaaa acacccagtt tttgttttta attcggcaag      600
tattgttgca atgtgtcttc gggccatttt gaatatagtg accatatgca gcaatagcta      660
cagtatcctg gttaattacg ggtttatctt aaacatggtt catatgtatg tccatgtgtt      720
taatatttta atttttgttgc ttgcaccggt catcattttt actgctgaga tgagcatgat      780
gattcaagtt cgtataattt gtgcacatga tagaaagaca caaggataa tgactgttat      840 tagtgcctgc ttaactgttt tggttctcgc attttggatt actaacatgt gtcaacagat      900
tcagtatctg ttatggttaa ctccacttag cagcaagacc attgttggat actcttggcc      960
ctactttatt gctaaaatac ttttgcttt tagcattatt tttcacagtg gtgttttttc     1020
atacaaactc tttcgtgcca tattaatacg gaaaaaaatt gggcaatttc catttggtcc     1080
gatgcagtgt attttagtta ttagctgcca atgtcttatt gttccagcta cctttactat     1140
aatagatagt tttatccata cgtatgatgg ctttagctct atgactcaat gtctgctaat     1200
catttctctt cctctttcga gtttatgggc gtctagtaca gctctgaaat tgcaaagcat     1260
```

```
gaaaacttca tctgcgcaag gagaaaccac cgaggtttcg attagagttg atagaacgtt    1320
tgatatcaaa catactccca gtgacgatta ttcgatttct gatgaatctg aaactaaaaa    1380
gtggacgtaa cttacgcctg aatgtatctt ttttgataat tcctaatact ggctcaataa    1440
cagtcccaaa taacatagac ggttttttta cgataggctt gtaatcataa tttgctcaga    1500
gggaagtttt ctaatggttt tttttttttc gcttcatgaa caattgttta ctataaacat    1560
caatgaaatt atatgattat aataacttat tatcatgaaa acttcaagtc gtacttcaca    1620
aacacttatt aaaacaatag tgaatgaact gccttcgtaa tctataatga actataatgt    1680
tttgagtctc caagtgctta ccttacgaac tttttttttt atttaaagct t             1731
```

<210> SEQ ID NO 29
<211> LENGTH: 348
<212> TYPE: PRT
<213> ORGANISM: Schizosaccharomyces pombe

<400> SEQUENCE: 29

```
Met Arg Gln Pro Trp Trp Lys Asp Phe Thr Ile Pro Asp Ala Ser Ala
 1               5                  10                  15

Ile Ile His Gln Asn Ile Thr Ile Val Ser Ile Val Gly Glu Ile Glu
             20                  25                  30

Val Pro Val Ser Thr Ile Asp Ala Tyr Glu Arg Asp Arg Leu Leu Thr
         35                  40                  45

Gly Met Thr Leu Ser Ala Gln Leu Ala Leu Gly Val Leu Thr Ile Leu
     50                  55                  60

Met Val Cys Leu Leu Ser Ser Glu Lys Arg Lys His Pro Val Phe
 65                  70                  75                  80

Val Phe Asn Ser Ala Ser Ile Val Ala Met Cys Leu Arg Ala Ile Leu
                 85                  90                  95

Asn Ile Val Thr Ile Cys Ser Asn Ser Tyr Ser Ile Leu Val Asn Tyr
            100                 105                 110

Gly Phe Ile Leu Asn Met Val His Met Tyr Val His Val Phe Asn Ile
        115                 120                 125

Leu Ile Leu Leu Leu Ala Pro Val Ile Ile Phe Thr Ala Glu Met Ser
    130                 135                 140

Met Met Ile Gln Val Arg Ile Ile Cys Ala His Asp Arg Lys Thr Gln
145                 150                 155                 160

Arg Ile Met Thr Val Ile Ser Ala Cys Leu Thr Val Leu Val Leu Ala
                165                 170                 175

Phe Trp Ile Thr Asn Met Cys Gln Gln Ile Gln Tyr Leu Leu Trp Leu
            180                 185                 190

Thr Pro Leu Ser Ser Lys Thr Ile Val Gly Tyr Ser Trp Pro Tyr Phe
        195                 200                 205

Ile Ala Lys Ile Leu Phe Ala Phe Ser Ile Ile Phe His Ser Gly Val
    210                 215                 220

Phe Ser Tyr Lys Leu Phe Arg Ala Ile Leu Ile Arg Lys Lys Ile Gly
225                 230                 235                 240

Gln Phe Pro Phe Gly Pro Met Gln Cys Ile Leu Val Ile Ser Cys Gln
                245                 250                 255

Cys Leu Ile Val Pro Ala Thr Phe Thr Ile Ile Asp Ser Phe Ile His
            260                 265                 270

Thr Tyr Asp Gly Phe Ser Ser Met Thr Gln Cys Leu Leu Ile Ile Ser
        275                 280                 285

Leu Pro Leu Ser Ser Leu Trp Ala Ser Ser Thr Ala Leu Lys Leu Gln
```

```
                            290               295               300
            Ser Met Lys Thr Ser Ser Ala Gln Gly Glu Thr Thr Glu Val Ser Ile
            305               310               315               320

Arg Val Asp Arg Thr Phe Asp Ile Lys His Thr Pro Ser Asp Asp Tyr
                              325               330               335

Ser Ile Ser Asp Glu Ser Glu Thr Lys Lys Trp Thr
                        340               345

<210> SEQ ID NO 30
<211> LENGTH: 984
<212> TYPE: DNA
<213> ORGANISM: Rattus norvegicus
<220> FEATURE:
<221> NAME/KEY: misc_feature
<222> LOCATION: (1)...(984)
<223> OTHER INFORMATION: n = A,T,C or G

<400> SEQUENCE: 30
atggagcgaa ggaaccacag tgggagagtg agtgaatttg tgttgctggg tttcccagct         60
cctgccccac tgcgagtact actatttttc ctttctcttc tggnctatgt gttggtgttg        120
actgaaaaca tgctcatcat tatagcaatt aggaaccacc caaccctcca caaacccatg        180
tattttttct tggctaatat gtcatttctg gagatttggt atgtcactgt tacgattcct        240
aagatgctcg ctggcttcat tggttccaag agagaaccat gacagctgat ctcctttgag        300
gcatgcatga cacaactcta cttttttcct ggcttgggtt gcacagagtg tgtccttctt        360
gctgtgatgg cctatgaccg ctatgtggct atctgtcatc cactccacta ccccgtcatt        420
gtcagtagcc ggctatgtgt gcagatggca gctggatcct gggctggagg ttttggtatc        480
tccatggtta aagttttcct tatttctcgc ctgtcttact gtggcccaa caccatcaac         540 cacttttcct gtgatgtgtc tccattgctc aacctgtcat gcactgacat gtccacagca        600
gagcttacag actttgtcct ggccattttt attctgctgg accgctctc tgtcactggg         660 gcatcctaca tggccatcac aggtgctgtg atgcgcatcc cctcagctgc tggccgccat        720
aaagcctttt caacctgtgc ctcccacctc actgttgtga tcatcttcta tgcagccagt        780
attttcatct atgccaggcc taaggcactc tcagcttttg acaccaacaa gctggtctct        840
gtactctacg ctgtcattgt accgttgttc aatcccatca tctactgctt gcgcaaccaa        900
gatgtcaaaa gagcgctacg tcgcacgctg cacctggccc aggaccagga ggccaatacc        960
aacaaaggca gcaaaattgg ttag                                               984

<210> SEQ ID NO 31
<211> LENGTH: 327
<212> TYPE: PRT
<213> ORGANISM: Rattus norvegicus
<220> FEATURE:
<221> NAME/KEY: VARIANT
<222> LOCATION: (1)...(327)
<223> OTHER INFORMATION: Xaa = Any Amino Acid

<400> SEQUENCE: 31

Met Glu Arg Arg Asn His Ser Gly Arg Val Ser Glu Phe Val Leu Leu
  1               5                  10                  15

Gly Phe Pro Ala Pro Ala Pro Leu Arg Val Leu Leu Phe Phe Leu Ser
                 20                  25                  30

Leu Leu Xaa Tyr Val Leu Val Leu Thr Glu Asn Met Leu Ile Ile Ile
            35                  40                  45

Ala Ile Arg Asn His Pro Thr Leu His Lys Pro Met Tyr Phe Phe Leu
```

```
                 50                  55                  60
Ala Asn Met Ser Phe Leu Glu Ile Trp Tyr Val Thr Val Thr Ile Pro
 65                  70                  75                  80

Lys Met Leu Ala Gly Phe Ile Gly Ser Lys Glu Asn His Gly Gln Leu
                 85                  90                  95

Ile Ser Phe Glu Ala Cys Met Thr Gln Leu Tyr Phe Leu Gly Leu
                100                 105                 110

Gly Cys Thr Glu Cys Val Leu Ala Val Met Ala Tyr Asp Arg Tyr
                115                 120                 125

Val Ala Ile Cys His Pro Leu His Tyr Pro Val Ile Val Ser Ser Arg
130                 135                 140

Leu Cys Val Gln Met Ala Ala Gly Ser Trp Ala Gly Phe Gly Ile
145                 150                 155                 160

Ser Met Val Lys Val Phe Leu Ile Ser Arg Leu Ser Tyr Cys Gly Pro
                165                 170                 175

Asn Thr Ile Asn His Phe Cys Asp Val Ser Pro Leu Leu Asn Leu
                180                 185                 190

Ser Cys Thr Asp Met Ser Thr Ala Glu Leu Thr Asp Phe Val Leu Ala
                195                 200                 205

Ile Phe Ile Leu Leu Gly Pro Leu Ser Val Thr Gly Ala Ser Tyr Met
210                 215                 220

Ala Ile Thr Gly Ala Val Met Arg Ile Pro Ser Ala Ala Gly Arg His
225                 230                 235                 240

Lys Ala Phe Ser Thr Cys Ala Ser His Leu Thr Val Val Ile Ile Phe
                245                 250                 255

Tyr Ala Ala Ser Ile Phe Ile Tyr Ala Arg Pro Lys Ala Leu Ser Ala
                260                 265                 270

Phe Asp Thr Asn Lys Leu Val Ser Val Leu Tyr Ala Val Ile Val Pro
                275                 280                 285

Leu Phe Asn Pro Ile Ile Tyr Cys Leu Arg Asn Gln Asp Val Lys Arg
290                 295                 300

Ala Leu Arg Arg Thr Leu His Leu Ala Gln Asp Gln Glu Ala Asn Thr
305                 310                 315                 320

Asn Lys Gly Ser Lys Ile Gly
                325

<210> SEQ ID NO 32
<211> LENGTH: 3088
<212> TYPE: DNA
<213> ORGANISM: Homo sapiens

<400> SEQUENCE: 32
atgggcggcg agtggggagc ggggccggga gtggagcagc cgccgcggcg gactggaccg      60
agcctcgccg gcgcgcacct gcccgcagcg cccgcggacg cgcagcgcgg cccgagcgcg     120
acgacctgcc gagcggcggc cgaggcggcg gtgtgggcgc gtcaggccgc gacgagggcg     180
ctgagacaaa tttacatgta ttggagacca gaccagaagc ccttctgaat taagatctca     240
cattcttgaa ggtggcattg aagagcacta agatcggaag atgagtgagc ttgaccagtt     300
acggcaggag gccgagcaac ttaagaacca gattcgagac gccaggaaag catgtgcaga     360
tgcaactctc tctcagatca caacaacat cgacccagtg ggaagaatcc aaatgcgcac     420
gaggaggaca ctgcggggc acctggccaa gatctacgcc atgcactggg gcacagactc     480
caggcttctc gtcagtgcct cgcaggatgg taaacttatc atctgggaca gctacaccac     540
```

```
caacaaggtc cacgccatcc ctctgcgctc ctcctgggtc atgacctgtg catatgcccc      600
ttctgggaac tatgtggcct gcggtggcct ggataacatt tgctccattt acaatctgaa      660
aactcgtgag gggaacgtgc gcgtgagtcg tgagctggca ggacacacag gttacctgtc      720
ctgctgccga ttcctggatg acaatcagat cgtcaccagc tctggagaca ccacgtgtgc      780
cctgtgggac atcgagaccg ccagcagac gaccacgttt accggacaca ctggagatgt      840
catgagcctt tctcttgctc ctgacaccag actgttcgtc tctggtgctt gtgatgcttc      900
agccaaactc tgggatgtgc gagaaggcat gtgccggcag accttcactg ccacgagtc      960 tgacatcaat gccatatgct tctttccaaa tggcaatgca tttgccactg gctcagacga     1020
cgccacctgc aggctgtttg accttcgtgc tgaccaggag ctcatgactt actcccatga     1080
caacatcatc tgcgggatca cctctgtctc cttctccaag agcgggcgcc tcctccttgc     1140
tgggtacgac gacttcaact gcaacgtctg ggatgcactc aaagccgacc gggcaggtgt     1200
cttggctggg catgacaacc gcgtcagctg cctgggcgtg actgacgatg catggctgt     1260 ggcgacaggg tcctgggata gcttcctcaa gatctggaac taacgccagt agcatgtgga     1320
tgccatggag actggaagac cattccaact tggacgcgtt accatgagag ccaaccgtac     1380
taacgtgaca accctacacc tcccctcaga acttcaaaag ggcaagatct ttttccttc     1440 acttattgct catatcctat gaaaccaaga gcacaattcc cattgagaga agatctctg     1500 tgctgtaaac taaaacaaat tgtgcattcc ttccggggcc atcgtctttg ttttctttt     1560 tgtcttgaat gaattttaaa aggaaatata aataaaaat gttaaccaga aggtaaactt     1620
gagtgtaatt gtcagacaga cacacttttc caccagtgta tttgaatttt agaccagtga     1680
ccctgttttg tggcattcat gcaaaacatg ctgagggctt tgttcatctg gtcatcgtgt     1740
ccaaatttca gtcatgtttg tagcaagatt ttggaagcat tcatatttcc tttttaaaat     1800
gtattccttt gtgttcaaca gttaatcaaa accagagagt ctagggcagc ctctctgatg     1860
ttgtcaatga tgtaaattca gtccctggtt tttaattttc tgtctgatgt cacagatcat     1920
tgttgcacac aaacgtggca tagaaaagaa catgttcaga agccatgggg ccaagcacaa     1980
tgcggggacg gtctcaaaat gcgtgatcag agaatccttc accttatgct gaaaagtgag     2040
ctcagatcca cctccaatgt tcctcctgac ccatcctgtc tatcttctca gttgagtttt     2100
taatctcact ttgggtttcc ttgtgaagtt ggagggaagt ttataatagc ctaacactac     2160
cccaccccca actaggagga acctctgttt tcaagagaga tgcctgtcct gtgcttggat     2220
agtcagtcaa ttatttgtgt atgaaacaat gtacaaatca atgttttgaa aataatgatc     2280
tcagactttc taagttaaag ttttaaaaat tttgattgtt tgccatattg ggtgggttta     2340
ctcttagaat cgcatgctgt agaaaatgct caaaagtgca tatgggactc agtccttagg     2400
tgttcttttt cttttaagaa ataaccctctt acagttgtaa ccattgcggc tctgtccact     2460
tctcgttgct gctctgtggc acatatcgga agcagtacag cgcgcggctc tacacgcttg     2520
ggtagcggga taagtcactg ttttctttat tctttaaaa aaaaaaaaag ttctgttgca     2580
aacgactgct gttggattct gagggtgggg agggagagag agggagggag agggagtgaa     2640
gagcctgccc tcctatagtg gattcttcac gggccctcca catctgaggt ggctcattcc     2700
catcacacac agattgtcct ggtgttcatt tcaaggccag ttgtcagcag cagcgtttgg     2760
aaagcaggtt ctgtgggacc cccgccccg ccccccgcac tccttcatag cagcagtagt     2820
```

```
ggcttctcca tcctgttttc tgcaacattc tatacaaaac tgtgctgtga ccttgcggta   2880
ggcctggatc tggcaaagag aatacaaatg aaaccccttc tttctctttc cgtccaacaa   2940
ctctgtagag ctctctgcac ccttacccct ttccacctt tgtatttaat tttaaagtca    3000
gtgtactgca aggaagctgg atgcaagata gatactatat taaactgtac tgttatttaa   3060
gatgtaataa agcagtttga catgaggg                                      3088
```

<210> SEQ ID NO 33
<211> LENGTH: 340
<212> TYPE: PRT
<213> ORGANISM: Homo sapiens

<400> SEQUENCE: 33

```
Met Ser Glu Leu Asp Gln Leu Arg Gln Glu Ala Glu Gln Leu Lys Asn
 1               5                  10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
    290                 295                 300

Ala Gly Val Leu Ala Gly His Asp Asn Arg Val Ser Cys Leu Gly Val
305                 310                 315                 320
```

```
Thr Asp Asp Gly Met Ala Val Ala Thr Gly Ser Trp Asp Ser Phe Leu
                325                 330                 335
Lys Ile Trp Asn
        340

<210> SEQ ID NO 34
<211> LENGTH: 702
<212> TYPE: DNA
<213> ORGANISM: Homo sapiens
<220> FEATURE:
<221> NAME/KEY: misc_feature
<222> LOCATION: (1)...(702)
<223> OTHER INFORMATION: n = A,T,C or G

<400> SEQUENCE: 34
ttccacaagg ttgggagcca acaatagtaa gattcagtgg cagtttttat gaattcagag      60
cattgtgcca aggcacattg tcaaaatgtc tgaaaattta ttttaatgtc agcaacaaaa     120
ttattcattc attgaagaaa tatttactga gggaatacta tatgtcaggt accaatacac     180
acattgcctg ctataaagtt tgtatcatca atgtatagga atgctggtat tcctgagccc     240
ttctaatagc atcttaaaaa tgatatttag cggccccgcc gacccacggc ccacgaccca     300
ccgacccacg aatcggcccg gccccgcgt tcaccatgtc tggcttctcc agcgtcgccg     360
ctacgaagaa agtggttcaa cagctccagc tggaggccgg gctcaacagc gtaaaagttt     420
cccaggcagc tgcagacttg aaacaattct gtctgcagaa tgctcaacat gaccctctgc     480
tgactggagt atcttcaagt acaaatccct tcagacccca gaaagtctgt tccttttgt     540 agtacaatga atctttcaaa ggtttcccaa accacttctt atgatccagt gaatattcaa     600
gagagataca tttgaagcct gtacaaaagc ttatccctgt aacacatgtg ctgtaatata     660
caaaattcta cttttgtcng tccttaacat ctacctctga at                       702

<210> SEQ ID NO 35
<211> LENGTH: 68
<212> TYPE: PRT
<213> ORGANISM: Homo sapiens

<400> SEQUENCE: 35

Met Ser Gly Phe Ser Ser Val Ala Ala Thr Lys Lys Val Val Gln Gln
1               5                   10                  15

Leu Gln Leu Glu Ala Gly Leu Asn Ser Val Lys Val Ser Gln Ala Ala
            20                  25                  30

Ala Asp Leu Lys Gln Phe Cys Leu Gln Asn Ala Gln His Asp Pro Leu
        35                  40                  45

Leu Thr Gly Val Ser Ser Thr Asn Pro Phe Arg Pro Gln Lys Val
    50                  55                  60

Cys Ser Phe Leu
65
```

BIOSENSOR FOR DEFECTING CHEMICAL AGENTS

CROSS-REFERENCE TO RELATED APPLICATION

This application claims the priority of copending U.S. Provisional Application Ser. No. 60/267,223 filed Feb. 8, 2001, the entire disclosure of which is herein incorporated by reference.

REFERENCE TO GOVERNMENT GRANT

The invention described herein was supported in part by the Department of Advance Research Agency (DARPA) of the Department of Defense, under grant no. N66001-00-C-8050. The government has certain rights in this invention.

FIELD OF THE INVENTION

This invention pertains to the field of molecular biosensors, in particular biosensors containing cloned olfactory receptors.

BACKGROUND OF THE INVENTION

The olfactory receptors are a class of G-protein coupled receptors (GPCR) found in the membranes of cells in olfactory or other sensing organs. The olfactory receptor proteins are considered the largest sub-family of GPCR; it has been estimated that human olfactory epithelium contains approximately 2000-3000 distinct olfactory receptors, whereas insects such as Drosophila have 100-200 such receptors. It is believed that any given olfactory or sensory cell contains one or a few types of olfactory receptors.

Olfactory receptor proteins have a distinctive structure of seven hydrophobic segments that span the cell membrane (trans-membrane domains I-VII), separated by hydrophilic segments which project into the intra- or extra-cellular space. Transmembrane domains II through VII comprise a hypervariable segment which defines the ligand specificity of the receptor. This hypervariable segment is flanked by hydrophobic consensus sequences. Furthermore, it is known that the N-terminal segment of the olfactory receptor is involved in receptor stability and the C-terminal segment is involved in G-protein coupling and activation. The structural organization of a typical olfactory receptor is given in FIG. 1.

The basic olfactory signaling unit consists of an olfactory receptor, a signal transducer (e.g., G-protein), an effector (e.g., adenylyl cyclase), second messengers (e.g., cAMP), and a gated channel (e.g., a calcium channel) as depicted in FIG. 2. Olfactory receptor signaling is not, however, limited to the G-protein-adenylyl cyclase-cAMP pathway; there is evidence of olfactory receptor signaling via G-protein activation of phosphoinositidase C, with subsequent production of inositol 1,4,5-triphosphate and 1,2-diacylglycerol second messengers.

The method of chemical detection by olfactory receptors is conserved among species. Upon activation by an olfactant, an olfactory receptor initiates a cellular signaling cascade that results in the influx of calcium ions, which in turn leads to a depolarization of a connected sensory neuron. The time from receptor activation by binding of ligand to calcium influx is typically a few milliseconds.

The olfactory receptors are highly sensitive and selective; for example, they can detect femtomolar concentrations ($10^{-13}$ M) of a specific chemical molecule and distinguish between two molecules differing in a single hydrogen atom.

The great variety, exquisite specificity and sensitivity, and fast-acting properties of the olfactory receptors make them ideal components of a biosensor. As its name implies, a biosensor is a detector that has a biological sensory component, such as a receptor protein or nucleic acid. Biosensors offer the advantages of higher resolution and the possibility of real-time monitoring of environments over conventional analytical techniques.

Also, because a biosensor can be constructed at the cellular or molecular level, many biosensors capable of detecting one or more substances can be contained in a very small area. Modem molecular biology and genetic techniques also allow a large number of diverse biological sensors to be generated quickly and cheaply.

However, several characteristics of typical eukaryotic expression systems, and of naturally occurring olfactory receptors, have prevented the production of a robust biological sensor that can be easily adapted to detect diverse substances. In particular, cloning and expression of olfactory receptors has been inhibited by the inability of many host cells to properly process and transport the receptors to the cell membrane.

Even if the olfactory receptors are properly positioned by the host cell, they are often not coupled to an appropriate second-messenger system. Coupling of olfactory receptors to their effectors appears to be highly specific, and endogenous G-proteins in heterologous host cells may not efficiently transduce and amplify the olfactory receptor's signal upon ligand binding. To overcome this shortcoming, host cells such as melanophores expressing large numbers of endogenous $G_{alpha}$ subunits (thus increasing the probability of an effective coupling) are often used. See TS McClintock et al. (1997), Molec. Brain Res. 48: 270-278. Alternatively, $G_{alpha}$ subunits which couple to a variety of receptors, such as the $G_{\alpha 15,16}$ subunits, are co-transfected into the host cell with the olfactory receptor. See Offermans and Simon (1995), J. Biol. Chem. 270(25): 15175-15180. However, such techniques do not reliably couple every olfactory receptor to a second-messenger.

Moreover, eukaryotic expression systems typically consist of cultured mammalian cells. Such systems are not robust, and require specialized handling under laboratory culture conditions to be viable.

The increasing threat of chemical and biological warfare agents in war and terrorist acts requires a biosensor that can operate in urban areas and battlefields alike under field conditions. The biosensor must be portable, rugged, sensitive, and reliable. What is needed, therefore, is a biosensor that can operate under the environmental conditions expected to be encountered outside the laboratory, and which reliably and reproducibly detects olfactants of interest.

BRIEF DESCRIPTION OF THE DRAWINGS

FIG. 6 shows black-and-white representations of laser confocal micrographs showing expression of GFP in WIF-1α-RI7 cells that were A) not exposed to any olfactant (None) or exposed to B) 100 nmoles of hexaldehyde (6-CHO); C) 100 nmoles heptaldehyde (7-CHO); or D) 100 nmoles of octaldehyde (8-CHO).

DEFINITIONS

Figure 1:
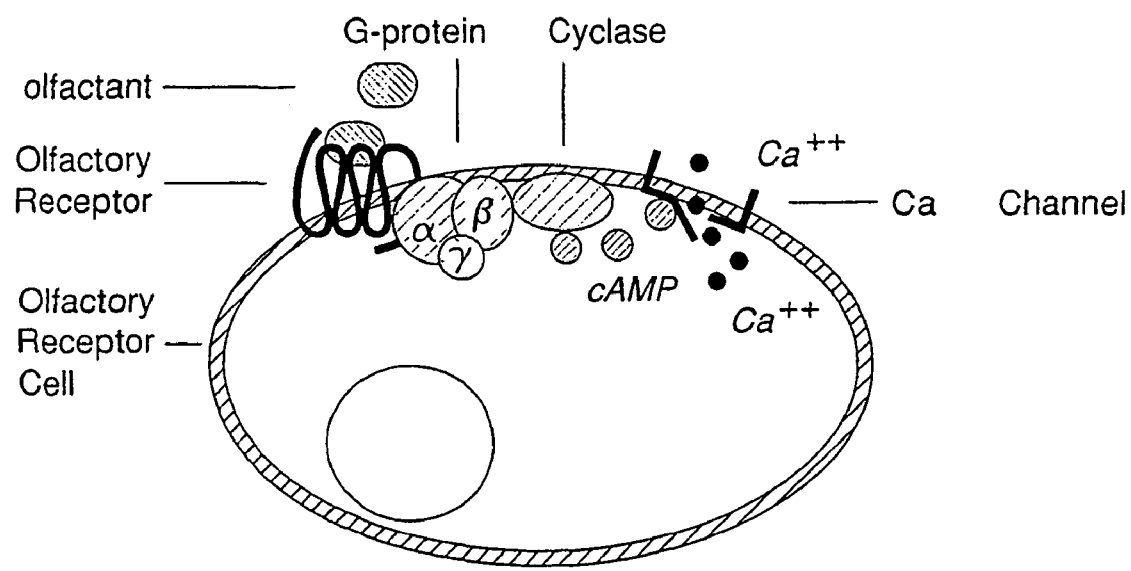
FIG. 1 shows the structural organization of a typical olfactory receptor.
Figure 2:
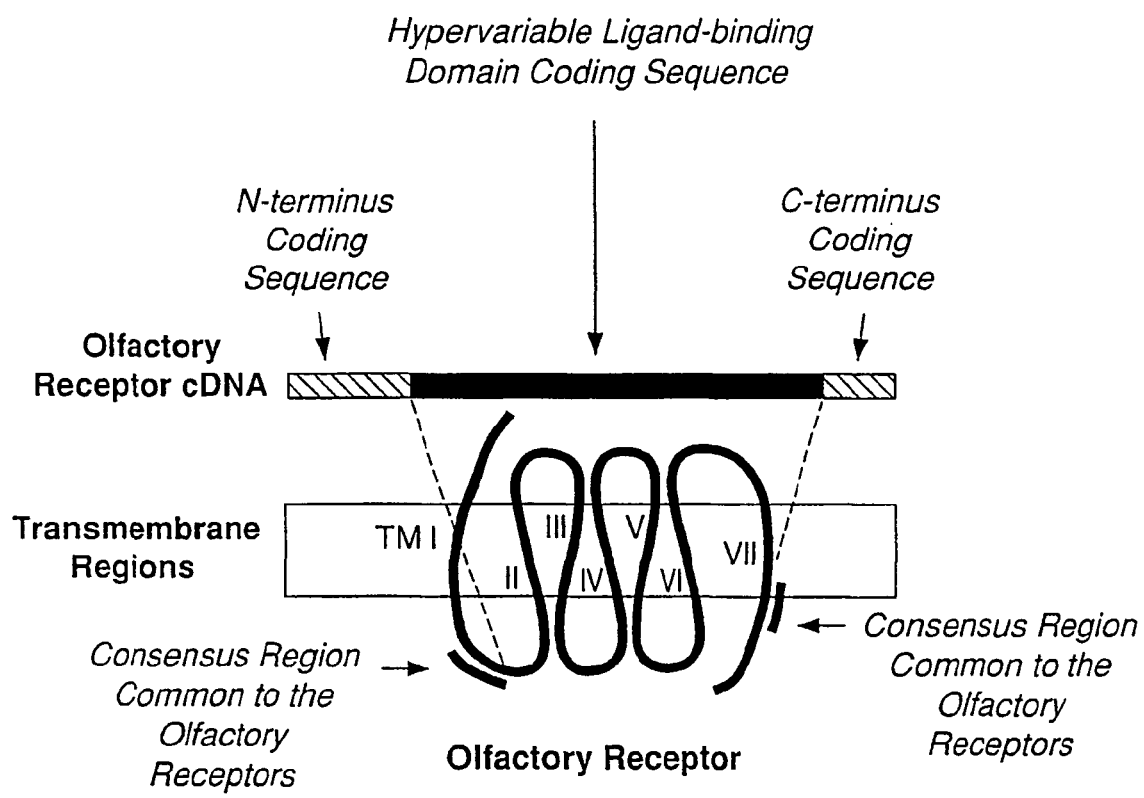
FIG. 2 shows the basic olfactory signaling unit.

The following definitions are provided to aid in the understanding of the invention:

As used herein, the term "chimeric protein" refers to two or more nucleotide sequences obtained from different genes that have been cloned together and that encode a single polypeptide segment. Chimeric proteins are also referred to as "hybrid proteins." As used herein, the term "chimeric protein" refers to coding segments that are obtained from different species of organisms, as well as coding segments that are obtained from the same species of organisms.

As used herein, "conservative amino acid substitutions" are substitutions with an amino acid which has a related side chain R. Amino acids are typically classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

As used herein, or "couples" or "coupling" refers to the physical and/or functional connection between two components of a cellular pathway or system. For example, the C-terminal segment of an olfactory receptor couples the receptor to the G-protein, allowing the activation of the G-protein upon binding of ligand to the receptor. The olfactory receptor C-terminal segment is an example of a "coupling segment," which is a segment of a protein or other cellular component that couples to another component.

As used herein, the term "cloning cassette" refers to a nucleic acid sequence that contains multiple cloning sites (i.e., "restriction sites," "MCS," or "polylinker"). It is intended that the term encompass DNA that contains unique, as well as non-unique restriction sites.

As used herein, "encoding" or "encoded" with respect to a specified nucleic acid means the genetic information contained within the nucleic acid may be translated into a specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum* (Proc. Natl. Acad. Sci. (USA), 82: 2306-2309 (1985)), or the ciliate *Macronucleus*, may be used when the nucleic acid is expressed using these organisms.

As used herein, the terms "express" or "expression" mean the production of a functional protein product from the genetic information contained within a nucleic acid sequence.

As used herein, "expression cassettes" are DNA constructs that include, 5' to 3' in the direction of transcription, a promoter, a DNA sequence operatively associated with the promoter, and, optionally, a termination sequence including a stop signal for RNA polymerase and a polyadenylation signal for polyadenylase. All of these regulatory regions should be capable of operating in the cell to be transfected. Suitable termination signals for a given DNA construct will be apparent to those of skill in the art. The term "operatively associated," as used herein, refers to the relationship between DNA sequences in a single DNA molecule which are associated so that the function of one sequence is affected by the other. Thus, a promoter is operatively associated with a DNA when it is capable of affecting the transcription of that DNA (i.e., the DNA is under the transcriptional control of the promoter). The promoter is upstream (5') from the DNA, which is in turn said to be downstream (3') from the promoter.

An expression cassette may be provided in a vector construct which also has at least one replication system. For convenience, it is common to employ a replication system functional in *Escherichia coli*, such as ColE1, pSC101, pACYC184, the pUC plasmids, or the like. In this manner, at each stage after each manipulation, the resulting construct may be cloned, sequenced, and the correctness of the manipulation determined. In addition, or in place of an *E. coli* replication system, a broad host range replication system may be employed, such as the replication systems of the P-1 incompatibility plasmids, e.g., pRK290. In addition to the replication system, there will frequently be at least one marker present in an expression cassette, which may be useful in one or more hosts, or different markers for individual hosts. That is, one marker may be employed for selection in a prokaryotic host, while another marker may be employed for selection in a eukaryotic host. The markers may comprise protection against a biocide, such as antibiotics, toxins, heavy metals, or the like; may provide complementation, by imparting prototrophy to an auxotrophic host; or may provide a visible phenotype through the production of a novel compound in the host.

Various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are know to those skilled in the art, and are amply illustrated in the literature, as exemplified by J. Sambrook et al., Molecular Cloning, A Laboratory Manual (2d Ed. 1989) (Cold Spring Harbor Laboratory).

As used herein, "exogenous" refers to a substance (e.g., protein, DNA or RNA) or system (e.g., a second-messenger cell signaling pathway) which has been introduced into a cell or the cell's ancestor through the efforts of humans. Such substances or systems may be a copy of something naturally found in the cell being transformed, or a sequence which is not naturally found in the cell being transformed, or fragments thereof.

As used herein, the term "gene" refers to a DNA sequence that incorporates (1) upstream (5') regulatory signals including a promoter, (2) a coding segment specifying the product, protein or RNA of the gene, (3) downstream (3') regions including transcription termination and polyadenylation signals and (4) associated sequences required for efficient and specific expression.

As used herein, "Green Fluorescent Protein" or "GFP" refers to the various naturally occurring forms of GFP which can be isolated from natural sources, as well as artificially modified GFPs which retain the fluorescent abilities of native GFP.

As used herein, the term "heterologous" means the substances, systems and/or cells being referred to do not have the same origin; or, if from the same origin, are substantially modified from their native form by deliberate human intervention.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein, "olfaction" or "olfactory reception" means the detection of compounds by an olfactory receptor coupled to a cell signaling pathway. The compound detected is termed an "olfactant" and may be air-borne (i.e., volatile) or in solution.

The term "promoter" refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences. Suitable promoters will be apparent to those skilled in the art, and will vary depending upon the cell in which the DNA is to be expressed. Both inducible and constitutive promoters are contemplated for use in the present invention.

As used herein, "a regulatory element" from a gene is the DNA sequence which is necessary for the expression of the gene, such as a promoter or responsive element. In this invention, the term "operatively linked" means that a regulatory element can direct the expression of a linked DNA sequence.

As used herein, a "robust cell" is a cell which is viable outside of controlled laboratory culture conditions and can perform the biochemical reactions necessary for olfactory detection in the field and, if necessary, under environmental extremes. Robust cells include those comprising a living organism that can be taken into the field, for example nematode, fish or insect species.

As used herein, the terms "transfection" or "transfected" include reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). A cell has been "transfected" by exogenous or heterologous DNA when such DNA has been introduced inside the cell.

As used herein, "vector" includes reference to a nucleic acid used in transfection of a host cell and into which can be inserted a polynucleotide. Vectors are often replicons. Expression vectors permit transcription of a nucleic acid inserted therein.

As used herein, the term "host cell" refers to any cell transfected with a nucleic acid for expressing a protein product, or that cell's progeny. A transfected cell or its progeny is considered a "host cell" as long as the nucleic acid for expressing a protein product is present in the cell, whether the nucleic acid is integrated into the cell's genome or exists as an extrachromosomal element. As used herein, a "host master cell" refers to a host cell transfected to express at least one signaling pathway. It is understood that a variety of master host cells may be constructed using different signaling pathways. Host master cells are used to construct "pre-biosensors," which are master host cells transfected to express at least one signal reporters. It is understood that a variety of pre-biosensor cells may be constructed from a given master host cell by transfection with different signal reporter DNA. The pre-biosensor cells are used to construct the biosensors of the invention, by transfection of pre-biosensor cells with at least one expression vector comprising a chimeric olfactory receptor protein. Master host cells, pre-biosensor cells, and biosensors, and methods of making and using them are described more fully below.

As used herein, a "signaling pathway" refers to a system of cellular components that transduces the signal produced from the binding of a ligand to a membrane-bound receptor into a biological effect. For example, a signaling pathway may comprise an intracellular G-protein, its associated effector protein and a gated ion channel in the cell membrane. The effector protein may comprise an enzyme, such as a phosphorylase or cyclase, and may be integral with the G-protein. Typically, the G-protein is activated by the binding of ligand to a receptor. The activated G-protein in turn activates the effector to produce a second messenger. The second messenger produces some biological effect in the cell, such as upregulating gene transcription or opening a gated ion channel. The production of a second messenger is also considered a biological effect. As used herein, the signaling pathway does not include the membrane-bound receptor; the signaling pathway plus receptor is termed a "signaling unit." Signaling pathways are described in more detail below.

As used herein, a "signal reporter" refers to one or more substances in cell that are responsive to a biological effect produced by the activation of the signaling pathway, for example changes in the intracellular concentration of an ion or second messenger. The signal reporter may comprise an indicator that produces a detectable phenomenon (e.g., fluorescence, change in electric potential of the cell membrane, etc.), or may be an integrated system of components that combine to produce a detectable phenomenon. Signal reporters are described in more detail below.

Abbreviations

The following is a list of abbreviations used in the specification:
$Ca^{++}$—calcium ion
cAMP—cyclic adenosine monophosphate
CREB—cAMP-responsive element binding protein
CRE—cAMP responsive element
DNA—deoxyribonucleic acid
EDTA—ethylene diamine tetraacetic acid
FURA-2—1-[6-Amino-2-(5-carboxy-2-oxazolyl)-5-benzofuranyloxy]-2-(2-amino-5-methylphenoxy)ethane-N,N,N',N'-tetraacetic acid, penta-potassium salt
GFP—green fluorescent protein
Golf—olfactory receptor G-protein
GPCR—G protein coupled receptor
LiAc—lithium acetate
mM—millimolar mm—millimeter
mg—milligram
ng—nanogram
nm—nanometers
PCR—polymerase chain reaction
RT-PCR—reverse-transcription polymerase chain reaction
RNA—ribonucleic acid
TE—Tris/EDTA
x-gal-5-bromo-4 chloro-3-indolyl-b-D-galactopyranoside
Amino Acids—The standard one- and three-letter amino acid abbreviations are used, as set forth in the following schedule:

| A | Alanine | Ala |
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

The prefix "L-" preceding an amino acid abbreviation (e.g., "L-Trp") denotes the biologically active levorotatory isomer of the amino acid.

SUMMARY OF THE INVENTION

The present invention provides a biosensor comprising one or more host cells expressing at least one chimeric olfactory receptor protein for binding olfactant; at least one exogenous signaling pathway coupled to the at least one chimeric olfactory receptor for transducing a signal produced by the chimeric olfactory receptor upon olfactant binding; and at least one signal reporter coupled to the signaling pathway for producing a detectable phenomenon upon transduction of the olfactant binding signal by the signaling pathway. The chimeric olfactory receptor protein expressed by the biosensor comprises an olfactory receptor hypervariable segment which contains at least one olfactant binding site, a processing/transport segment which directs the processing and transport of the chimeric receptor in the host cell; and a coupling segment which couples the chimeric receptor to an exogenous signaling pathway in the host cell. In preferred embodiments, the expressed chimeric receptor comprises an N-terminal processing/transport signal segment and a C-terminal G-protein receptor coupling segment flanking an olfactory receptor hypervariable segment.

The invention also provides a library of biosensors comprising a plurality of biosensors with differing olfactant specificities.

The invention also provides host master cells, which are host cells transfected to express at least one exogenous signaling pathway.

The invention also provides a pre-biosensor comprising a host master cell of the invention further transfected to express at least one signal reporter.

The invention also provides a basic expression vector comprising a cloning cassette and nucleotide sequences encoding a processing/transport signal segment and a G-protein receptor coupling segment operative in an olfactory receptor protein. A nucleotide sequence encoding an olfactory receptor hypervariable segment may be inserted into the cloning cassette to produce an expression vector that can express a chimeric olfactory receptor protein. In preferred embodiments, the nucleotide sequences encoding an olfactory receptor hypervariable segment a coupling segment flank the cloning cassette.

The invention also provides an expression vector comprising nucleotide sequences encoding a chimeric olfactory receptor protein, wherein the receptor protein comprises (i) an olfactory receptor hypervariable segment which contains at least one olfactant binding site; (ii) a processing/transport segment which directs the processing and transport of the chimeric receptor in the host cell; and (iii) a coupling segment which couples the chimeric receptor to an exogenous signaling pathway in the host cell. In preferred embodiments, the chimeric receptor protein comprises (i) an olfactory receptor hypervariable segment; (ii) a processing/transport signal segment N-terminal to the olfactory receptor hypervariable segment; and (iii) a G-protein receptor coupling segment C-terminal to the olfactory receptor hypervariable segment.

The invention also provides an expression vector library comprising expression vectors which contain different olfactory receptor hypervariable segments. Such a library may be used to construct a library of biosensors with differing olfactant specificities.

The invention also provides a method of producing a biosensor, comprising transfecting one or more host cells to express (i) at least one chimeric olfactory receptor protein for binding olfactant; (ii) at least one exogenous signaling pathway coupled to the at least one chimeric olfactory receptor for transducing a signal produced by the chimeric olfactory receptor upon olfactant binding; and (iii) at least one signal reporter coupled to the signaling pathway for producing a detectable phenomenon upon transduction of the olfactant binding signal by the signaling pathway.

The invention further provides a method of identifying biosensors which can detect an olfactant, comprising the steps of providing at least one biosensor of the invention, wherein detection of the olfactant by the biosensor generates a detectable phenomenon from the signal reporter contacting the one or more biosensor with the olfactant; contacting the at least one biosensor with an olfactant, and observing whether the detectable phenomenon is produced from the signal reporter.

The invention further provides a method for detecting an olfactant in a sample, comprising the steps of providing one or more biosensors of the invention capable of detecting an olfactant, wherein detection of the olfactant by the biosensor generates a detectable phenomenon from the signal reporter; contacting the one or more biosensors with a sample suspected of containing the olfactant; and observing whether the detectable phenomenon is produced from the biosensor signal reporter.

The invention further provides an apparatus capable of detecting the detectable phenomenon produced by detection of an olfactant by a biosensor of the invention. The apparatus comprises a measurement tool for measuring the detectable phenomenon, means for controlling the measurement tool (e.g., a computer controller) and one or more biosensors of the invention preferably comprising an array or biochip.

The invention further provides kits comprising various combinations of the components for constructing the biosensors of the invention.

The invention further provides arrays and portable containers comprising biosensors of the invention.

DETAILED DESCRIPTION OF THE INVENTION

The present biosensors are designed for use in the field, under potentially harsh or changeable environmental conditions. As such, the biosensors are constructed from cells able to survive outside of the controlled environment of the laboratory for more than a limited time.

The present biosensors are therefore preferably constructed from robust cells. Robust cells useful in the invention may be obtained from any prokaryotic or eukaryotic organism which is adapted to live in a harsh or changeable environment. For example, some species of bacteria can exist in extremes of temperature (e.g., *Thermus aquaticus* and other thermophilic bacteria) in high-salt (e.g., halobacteria) or low-oxygen environments, under conditions of acidity or basicity, in high pressure, or combinations of these. Some eukaryotes, in particular the fungi, are also resistant to environmental extremes. For example, various species of psychrotropic fungi (i.e., *Humicola marvinii; H. fuscoatra*; see Weinstein et al., Mycologia, 1997, 89(5), p. 706-711) live in the fellfield soils of the maritime Antarctic, and the larva of the brine fly (*Ephydra*) is adapted for life in the pink salt lakes of California's Sierra Nevada mountains.

Robust cells may be employed as single-cell biosensors, or as part of a multi-celled organism that is taken into the field. For example, yeast cells comprising the appropriate olfactory detection and signaling components may be brought into the area to be tested for olfactants, or living organisms which have had one or all of their cells converted into biosensors may be used.

Robust cells useful in the biosensors and methods of the present invention therefore include prokaryotic cells such as bacterial cells, and eukaryotic cells including yeast cells, fungal cells, insect cells, nematode cells, and plant or animal cells. Biosensors constructed from eukaryotic cells may be single-cell or may comprise intact multicellular organisms, including nematodes (e.g., *Caenorhabditis elegans*), transparent or semi-transparent animals (e.g., zebrafish), and insects (e.g., *Drosophila*).

Yeast are perhaps the most well-known of the eukaryotes that are highly resistant to adverse environmental conditions. Yeast cells are resistant to radiation, wind shear, and dehydration damages. Their nutrient requirements are quite simple and minimal. In addition, yeast cells are genetically well characterized and thus are amenable to genetic manipulations. Furthermore, yeast cells have signaling pathways analogous to those of higher animals, and hence the cells can be genetically altered to express functional signaling units of higher animals. Yeast cells, in particular from strains of *Saccharomyces cerevisiae*, are preferred for constructing the present biosensors. For ease of discussion, the invention will be illustrated with reference to yeast; however, it is understood that other robust cells may be used.

The yeast cells may be transfected to contain one or more exogenous signaling pathways for transducing the signal produced by an olfactory receptor protein upon binding of an olfactant. Any G-protein signaling pathway may be used. In a preferred embodiment, the pathway comprises the G-protein-mediated activation of adenylate cyclase with resultant production of cAMP as a second messenger (see *The Encyclopedia of Molecular Biology*, [Kendrew J and Lawrence E, eds.], Blackwell Sciences, 1994, London, pp. 998-1003, herein incorporated by reference).

As shown in FIG. 1, a typical signaling unit comprises the olfactory receptor coupled to a signaling pathway comprising a G protein (e.g., an olfactory receptor G-protein, or Golf), adenylyl cyclase, the second messenger cyclic AMP (cAMP), and cAMP-activated cation channel. The G-protein consists of three subunits; the $G_{alpha}$ subunit (which dictates the coupling specificity) and $G_{beta}$ and $G_{gamma}$ subunits. A G-protein may comprise subunits from the same source; for example, alpha, beta and gamma subunits from a single species. Alternatively, a G-protein may comprise subunits from different sources; for example, alpha, beta and gamma subunits each from a different species, or an alpha subunit from one species and a beta and gamma subunit from a second species.

In a particularly preferred embodiment, the exogenous signaling pathway comprises the cAMP signal transduction pathway associated with a G-protein comprising the rat M4 olfactory G-protein (Golf) alpha subunit. See Jones D T and Reed R R (1989), Science 244, 790-795 and GenBank record accession No: M26718, the disclosures of which are herein incorporated by reference in their entirety. The rat M4 Golf alpha subunit may be associated with rat beta and gamma subunits to form the G-protein, or may be associated with beta and gamma subunits from other species (e.g., *Homo sapiens*) to form the G-protein.

The nucleotide and amino acid sequences for *H. sapiens* G-protein beta subunit are found in GenBank record accession no. X04526; see also Codina J et al. (1986) FEBS Lett. 207 (2), 187-192, the disclosures of which are herein incorporated by reference in their entirety. The nucleotide and amino acid sequences for *H. sapiens* G-protein gamma subunit are found in GenBank record accession no. AF188178; see also Hurowitz E H et al. (2000), DNA Res. 7 (2), 111-120, the disclosures of which are herein incorporated by reference in their entirety.

Binding of olfactant to the expressed olfactory receptor on the surface of the host cell sends a signal which activates the G-protein (for example, one comprising rat M4 Golf alpha subunit), which in turn stimulates adenylyl cyclase. The activated adenylyl cyclase catalyzes the formation of cyclic adenosine monophosphate (cAMP) which then opens a cAMP-gated cation (usually $Ca^{++}$) channel. The sequential activation of the G-protein and adenylate cyclase upon binding of an olfactant to the olfactory receptor is an example of signal transduction. That is, the signal produced by binding of olfactant to the receptor is transduced into a biological effect by activation of the G-protein and adenylate cyclase, with subsequent production of second messenger.

In situ, the resultant influx of $Ca^{++}$ can cause the depolarization of the olfactory neuron; in the present biosensors, the $Ca^{++}$ influx may activate a signal reporter. For ease of discussion, the invention will be illustrated with the G-protein/cAMP pathway. However, it is understood that any G-protein second messenger pathway may be transfected into the host cells.

A host master cell line may be constructed by the transfection, preferably sequential transfection, of genetic material encoding the non-variable components of the signaling pathway into the host cells. The invariant components include all factors necessary for coupling of the signaling pathway to the chimeric olfactory receptor, and for generation of the signal which results in cation (e.g., $Ca^{++}$) entry into the cell. For example, these components may comprise the G-protein subunits (α-, β-, and γ-subunits), type III adenylyl cyclase, and an endogenous or exogenous cation channel.

Preferably, the genetic material encoding the signaling pathway components comprises a plasmid vector. However, the genetic material may take any form suitable for introduction into a prokaryotic or eukaryotic cell which is known in the art, for example an artificial chromosome, viral vector, liposome encapsulated DNA, etc. Preferably, the genetic material stably integrates into the genome of the host cell, so that the exogenous signaling pathway components are present in subsequent generations.

Any suitable method may be used to transfect the host cells with the signaling pathway components. Transfection methods for prokaryotic cells are well known in the art, and are outlined, for example, in Molecular Cloning, a Laboratory Manual, supra. Transfection methods for eukaryotic cells are also well known in the art, and include, for example, direct injection into the nucleus or pronucleus, electroporation, liposome transfer and calcium phosphate precipitation. In a preferred method, the transfection is performed with a liposomal transfer compound, e.g., DOTAP (N-[1-(2,3-dioleoyloxy)propyl]-N,N,N-trimethylammonium methylsulfate, Boehringer-Mannheim) or an equivalent, such as LIPOFECTIN.

Techniques for isolating the signaling pathway components, insertion of these components into vectors for transfecting the host cells, and for stably transfecting the host cells are within the known to those of skill in the art. See generally Molecular Cloning, A Laboratory Manual (second edition) Ed. J. Sambrook, E. F. Fritsch, T. Maniatis (Cold Spring harbor Press. 1989). See also Jones D T and Reed R R (1989) supra; Codina J et al. (1986) supra; and Hurowitz E H et al. (2000), supra. Construction of exemplary signaling component vectors and the transfection of S. cerevisiae to produce the yeast host master cell WIF-1 are described in Example 1.

Following the transfection of each of the signaling pathway components into the host cell, expression of each component may be verified by reverse-transcription PCR (RT-PCR) as known to those skilled in the art, and as described in Example 1. The functionality of the transfected components may be tested using specific assays, for example assays designed to monitor the accumulation of cAMP in response to the activation of the olfactory signaling unit independent of receptor, as described in Example 5.

A host master cell line is converted into a "pre-biosensor" by transfection with a signal reporter, for example one responsive to intracellular levels of cAMP or Ca++. The signal reporter couples the detection of an olfactant by the biosensor to a detectable phenomenon that may be perceived by an observer. Preferred are signal reporters comprising CREB and CRE-driven GFP.

The detectable phenomenon from the signal reporter may comprise fluorescent signals, although those skilled in the art will appreciate that other indicia are known and may be used in the practice of the present invention, such as may be provided by labels that produce signals comprising, for example, visible light, fluorescence; radioactivity; colorimetry; X-ray diffraction or absorption; electricity or change in electric potential; or magnetism. Such labels include, for example, fluorophores, chromophores, radioactive isotopes (e.g., $^{32}P$ or $^{125}I$) and electron-dense reagents.

Fusion proteins comprising beta-galactosidase, firefly luciferase, and bacterial luciferase segments are also known methods of detecting gene expression and protein interactions in cells and are useful in the present invention. However, these methods require exogenously-added substrates or cofactors, and may not be convenient in a biosensor designed for use in the field. In the biosensors and methods of the present invention, therefore, an inherently fluorescent marker molecule is preferred, since detection of such a marker requires only the radiation by the appropriate wavelength of light and is not substrate limited. A preferred inherently fluorescent molecule is Green Fluorescent Protein, or GFP.

Green Fluorescent Protein (GFP) was first isolated from the jelly fish Aequorea victoria, and has an inherent green bioluminescence that can be excited optically by blue light or nonradiative energy transfer. Sequences of GFP-encoding cDNA, and GFP proteins are known; see, e.g., Prasher et al., Gene, 111:229 (1992), the disclosure of which is herein incorporated by reference. Purified native GFP absorbs blue light (maximally at 395 nm with a minor peak at 470 m) and emits green light (peak emission at 509 nm) (Morise et al, Biochemistry, 13:2656 (1974); Ward et al., Photochem. Photobiol., 31:611 (1980)). It has been shown that GFP expressed in prokaryotic and eukaryotic cells produces a strong green fluorescence when excited by near UV or blue light (see U.S. Pat. No. 5,491,084 to Chalfie and Prasher, herein incorporated by reference in their entirety). As this fluorescence requires no additional gene products from A. victoria, chromophore formation is not species-specific, and occurs either through the uses of ubiquitous cellular components or by autocatalysis. Expression of GFP in Escherichia coli results in an easily detected green fluorescence that is not seen in control bacteria. See Chalfie et al., Science 263:802 (1994); U.S. Pat. No. 5,491,084, supra.

As used herein, Green Fluorescent Protein or GFP refers to the various naturally occurring forms of GFP which can be isolated from natural sources, as well as artificially modified GFPs which retain the fluorescent abilities of native GFP. As discussed in Ormo et al., Science 273:1392 (1996), the disclosure of which is herein incorporated by reference, various mutants of GFP have been created with altered excitation and emission maxima. Additional alterations in the GFP protein sequence which provide inherently fluorescent, biologically compatible molecules will be apparent to those in the art; sequence alterations may be made to alter the solubility characteristics of the protein, its excitation wavelength, or other characteristics, while retaining useful fluorescent properties. See, e.g., U.S. Pat. No. 5,625,048 to Tsien and Heim; WO 9711091 (Bjorn, Poulsen, Thastrup and Tullin); WO 9627675 (Haseloff, Hodge, Prasher and Siemering); WO 9627027 (Ward); WO 9623898 (Bjorn et al.); WO 9623810 (Heim and Tsien); WO 9521191 (Chalfie and Ward), the disclosures of which are herein incorporated by reference in their entirety.

Preferably, the genetic material comprising the signal reporter comprises one or more plasmid vectors. However, the genetic material may take any form suitable for introduction into a prokaryotic or eukaryotic cell which is known in the art, for example an artificial chromosome, viral vector, liposome encapsulated DNA, etc. Preferably, the genetic material stably integrates into the genome of the host master cell, so that the signal reporter is present in subsequent generations.

Techniques for isolating or constructing the signal reporter, insertion into vectors for transfecting the host cells, and for transfecting the host cells are within the skill in the art, as discussed above. Construction of an exemplary signal reporter vector and the transfection yeast master strain WIF-1 to produce pre-biosensor strain WIF-1α are described in Example 2.

Following the transfection of the signal reporter into the host master cell line, expression may be verified by reverse-transcription PCR (RT-PCR) as known to those skilled in the art. The functionality of the reporter may be tested, for example, by assaying for the specific response expected from the signal pathway upon activation of the olfactory receptor signaling pathway, as described in Example 5.

Exemplary signal reporters include, for example:
1. Cyclic AMP-responsive GFP expression systems—In such systems, the cAMP generated in yeast cells upon detection of a specific molecule through the olfactory receptor activates "cAMP-responsive element binding protein" (CREB). The activated CREB in turn binds to a cAMP-responsive element (CRE) sequence of DNA that is operatively linked to nucleotide sequences encoding GFP (i. e., can drive the expression of GFP).
2. Cyclic AMP-responsive β-galactosidase expression systems—In such systems, the cAMP generated in yeast cells upon activation of the olfactory receptor activates CREB. The activated CREB in turn binds to a CRE sequence of DNA that can drive the expression of the bacterial lacZ gene (which encodes the β-galactosidase). When grown in the presence of X-Gal, the cells expressing β-galactosidase turn blue in color. Since β-galactosidase is expressed only in response to cAMP coupled to the olfactory receptor, the blue color identifies the detection of a specific molecule by the respective yeast colony. This system is useful if the immediate detection of olfaction is not desired, or is not possible, as the calorimetric response may take several hours to develop.
3. $Ca^{++}$-responsive luminescence reporter systems—For example, cDNAs encoding rat olfactory cell specific $Ca^{++}$ channel and photoprotein Apoaequorin of coelenterate jelly fish *Aequorea victoria* may be expressed in *S. cerevisiae*. The yeast may be grown in medium containing coelenterazine so that the $Ca^{++}$-sensitive aequorin is formed. Upon the influx of $Ca^{++}$ after activation of the olfactory receptor, aequorin binds to $Ca^{++}$ and emits blue light. This blue light can be read at 460-470 nm, for example in a luminescence bioassay plate reader.
4. Fluorescent cytosolic $Ca^{++}$ indicators—$Ca^{++}$ influx following the detection of a specific molecule through the olfactory receptor can be also monitored using any fluorescent cytosolic $Ca^{++}$ indicator, for example FURA-2-mediated $Ca^{++}$ fluorescence (510 nm).
5. Electrophysiological systems—Such systems comprise the electrophysiological detection of $Ca^{++}$ influx, for example by measuring the depolarization of the biosensor's cell membrane (or the membrane of an associated cell, such as a neuron). Such methods are known in the art. See, for example, U.S. Pat. No. 5,993,778 which describes the measurement of the change in cell-membrane potential of cells expressing olfactory receptors in situ with an (termed an "electro-olfactogram recording"). This method is easily adaptable to measure membrane potentials of biosensors located, for example, on an assay plate or array.

A pre-biosensor may be transfected with one or more expression vectors comprising an actual or putative hypervariable segment of an olfactory receptor to produce a biosensor. Transfection may be accomplished by any method designed to introduce genetic material into a prokaryotic or eukaryotic cell, as described above.

Multicellular organisms comprising biosensors may be produced by transfecting the signaling pathway components, signal reporter and an expression vector comprising an olfactory receptor hypervariable segment (see below) into a pluripotent stem cell, for example an embryonic stem cell, and allowing the transfected stem cell to develop into a mature organism. Such techniques are known in the art; see for example Thomson et al., (1998) Science 282:1145-47 and Reubinoff et al. (2000) Nat. Biotechnol. 18: 399-404 (both incorporated herein by reference). For example, chimeric animals may be produced by aggregation of altered stem cells with normal blastocyst cells and transgenic animals are recovered as offspring of the chimeric animals, according to the method of Capecchi, M. R., 1989, Science 244: 1288, the entire disclosure of which is incorporated herein by reference.

Alternatively, transfection of lower eukaryotes (e.g., *Caenorhabditis elegans*) to create multicellular organisms comprising biosensors may be performed by direct injection of genetic material into the germ cells or gonads, according to known techniques.

An expression vector transfected into the pre-biosensor may comprise an expression cassette comprising sequences encoding a chimeric olfactory receptor. The encoded chimeric olfactory receptor may comprise a processing/transport and G-protein receptor coupling segment operative in an olfactory receptor, and an olfactory receptor hypervariable segment. In preferred embodiments, the processing/transport and G-protein receptor coupling segments are N- and C-terminal to an olfactory receptor hypervariable segment, respectively. The processing/transport segment N-terminal to the olfactory receptor hypervariable region directs its processing and transport of the chimeric olfactory receptor, and the coupling segment C-terminal to the olfactory receptor hypervariable region couples the chimeric olfactory receptor to an exogenous signaling pathway in the pre-biosensor cell line.

The basic expression vector (i.e., the vector comprising a cloning cassette and nucleotide sequences encoding the processing/transport and coupling segments before addition of nucleotide sequences encoding an olfactory receptor hypervariable segment) is considered part of the present invention. Construction of an exemplary basic expression vector for yeast, comprising a cloning cassette and nucleotide sequences encoding processing/transport and coupling segments derived from the rat RI7 olfactory receptor is given in Example 4.

As the olfactory receptor hypervariable segment (i.e., transmembrane domains II-VII) is involved in ligand detection and discrimination, a library of expression vectors containing different olfactory receptor hypervariable segments may be constructed which encode chimeric olfactory receptors of different specificities. This expression library may then be used to construct a library of biosensors of differing specificity, which are then screened for the ability of individual biosensors of the library to detect an olfactant of interest.

The segment N-terminal to the hypervariable region of the chimeric olfactory receptor preferably comprises amino acid sequences derived from an olfactory receptor of the host cell species. For example, if the host master cell line is derived from *S. cerevisiae*, processing and transport segments from segments N-terminal to the hypervariable segment of a naturally occurring *S. cerevisiae* olfactory receptor may be used. An example of such a segment is the first 60 amino acids of the *S. pombe* mam2 pheremone receptor, represented below with the N-terminus to the left, and the C-terminus to the right:

```
(SEQ ID NO: 1)
MRQPWWKDFTIPDASAIIHQNITIVSIVGEIEVPVSTIDAYERD

RLLTGMTLSAQLALGV
```

The full length cDNA and protein translation of mam2 is given in SEQ ID NO: 28 and SEQ ID NO: 29, respectively, and in GenBank record accession no. X61672; see also Kitamura K and Shimoda C (1991), EMBO J. 10 (12), 3743-375, the disclosures of which are herein incorporated by reference in their entirety.

Processing/transport segments from another species' olfactory receptor may also be used if it is known or determined that the segments are operational in the host master cell line. For example, the inventors have discovered that the N-terminal 61 amino acids of the rat RI7 olfactory receptor, represented below with the N-terminus to the left, and the C-terminus to the right, allows the efficient processing and transport of a chimeric olfactory receptor in yeast host cells:

```
MERRNHSGRVSEFVLLGFPAPAPLRVLLFFLSLLXYVLVLTENMLIIIAIR    (SEQ ID NO: 2)

NHPTLHKPMY
```

The full length cDNA and protein translation for the rat RI7 olfactory receptor are given in SEQ ID NO: 30 and SEQ ID NO: 31, respectively. See also GenBank record accession no. M64386 and Buck and Axel (1991), Cell 65: 175-187, the disclosures of which are herein incorporated by reference in their entirety.

Thus, suitable processing/transport segments may be identified both structurally (i.e., they are located N-terminal to the hypervariable segment of olfactory receptor proteins) and functionally (i.e., they direct efficient processing and transport of the chimeric olfactory receptors to the host cell membrane).

The coupling segment C-terminal to the hypervariable segment of the chimeric olfactory receptor preferably comprises sequences derived from segments C-terminal to the hypervariable segment of an olfactory receptor known to couple efficiently with an exogenous signaling pathway transfected into the pre-biosensor cell line. Preferably, the coupling segment will comprise amino acid segments of olfactory receptors of the same species from which the exogenous signaling pathway was obtained. For example, for a yeast cell engineered with a rat signaling pathway comprising rat M4 Golf-mediated activation of adenylyl cyclase, the coupling segment of the chimeric receptor protein may comprise the last 35 amino acids of the rat RI7 olfactory receptor, represented below with the N-terminus to the left, and the C-terminus to the right:

```
IIYCLRNQDVKRALRRTLHLAQDQEANTNKGSKIG    (SEQ ID NO: 3)
```

Other coupling segments may also be used, if it is known or determined that they promote efficient coupling to the exogenous signaling pathway in the pre-biosensor.

Suitable coupling segments may therefore be identified both structurally (i.e., they are located C-terminal to the hypervariable segment of olfactory receptor proteins) and functionally (i.e., they couple the chimeric olfactory receptor to a specific G-protein second messenger pathway).

Variants of a given processing/transport or coupling segment may exist in nature or may be artificially produced. These variants may be allelic variations characterized by differences in the nucleotide sequences of the structural gene coding for the protein, or may involve differential splicing or post-translational modification. The skilled artisan can isolate or produce derivatives of an processing/transport or coupling segments having single or multiple amino acid substitutions, deletions, additions, or replacements. These derivatives may include, inter alia: (a) derivatives in which one or more amino acid residues are substituted with conservative or non-conservative amino acids, (b) derivatives in which one or more amino acids are added to the protein, (c) derivatives in which one or more of the amino acids includes a substituent group, and (d) derivatives in which the protein is fused with another peptide. The techniques for obtaining these derivatives, including genetic (suppressions, deletions, mutations, etc.), chemical, and enzymatic techniques, are known to persons having ordinary skill in the art.

The invention thus provides a chimeric olfactory receptor protein comprising an actual or putative olfactory receptor hypervariable segment and defined segments N- and C-terminal to the hypervariable segment, wherein the segment N-terminal to the hypervariable segment directs the efficient processing and transport of the chimeric receptor in the host cell, and the segment C-terminal to the hypervariable segment couples the chimeric receptor to an exogenous signaling pathway of the host cell.

In a preferred embodiment, the chimeric olfactory receptor comprises an olfactory receptor hypervariable segment, a yeast mam2 processing/transport segment N-terminal to the hypervariable segment, and a rat R17 receptor coupling segment C-terminal to the hypervariable region. The yeast mam2 segment may include the first 60 amino acids of the mam2 protein. The yeast mam2 segment ensures maximal expression and proper translocation of the chimeric olfactory receptor protein in yeast host cells, and the rat RI7 segment restricts the cell signaling interaction of the chimera to the exogenous Golf-mediated cAMP pathway of the yeast master cell. In a particularly preferred embodiment, the yeast mam2 segment is replaced by the N-terminal 61 amino acids comprising the processing/transport segment of the rat RI7 receptor (see Example 4).

Actual or putative hypervariable segments for cloning into the basic expression vector may be obtained by any method designed to isolate the nucleic acid sequences encoding transmembrane domains II through VII; for example, nuclease digestion of appropriate olfactory receptor genomic or cDNA sequences or PCR amplification of the hypervariable segment.

A preferred method is PCR amplification of transmembrane domains II-VII based on the flanking consensus amino acid sequences known to exist in olfactory receptors. See Buck and Axel (1991), Cell 65: 175-187; Krautwurst et al. (1998), Cell 95: 917-926 and Zhao et al. (1998), Science 279: 237-242, the disclosures of which are herein incorporated by reference.

Figure 3:
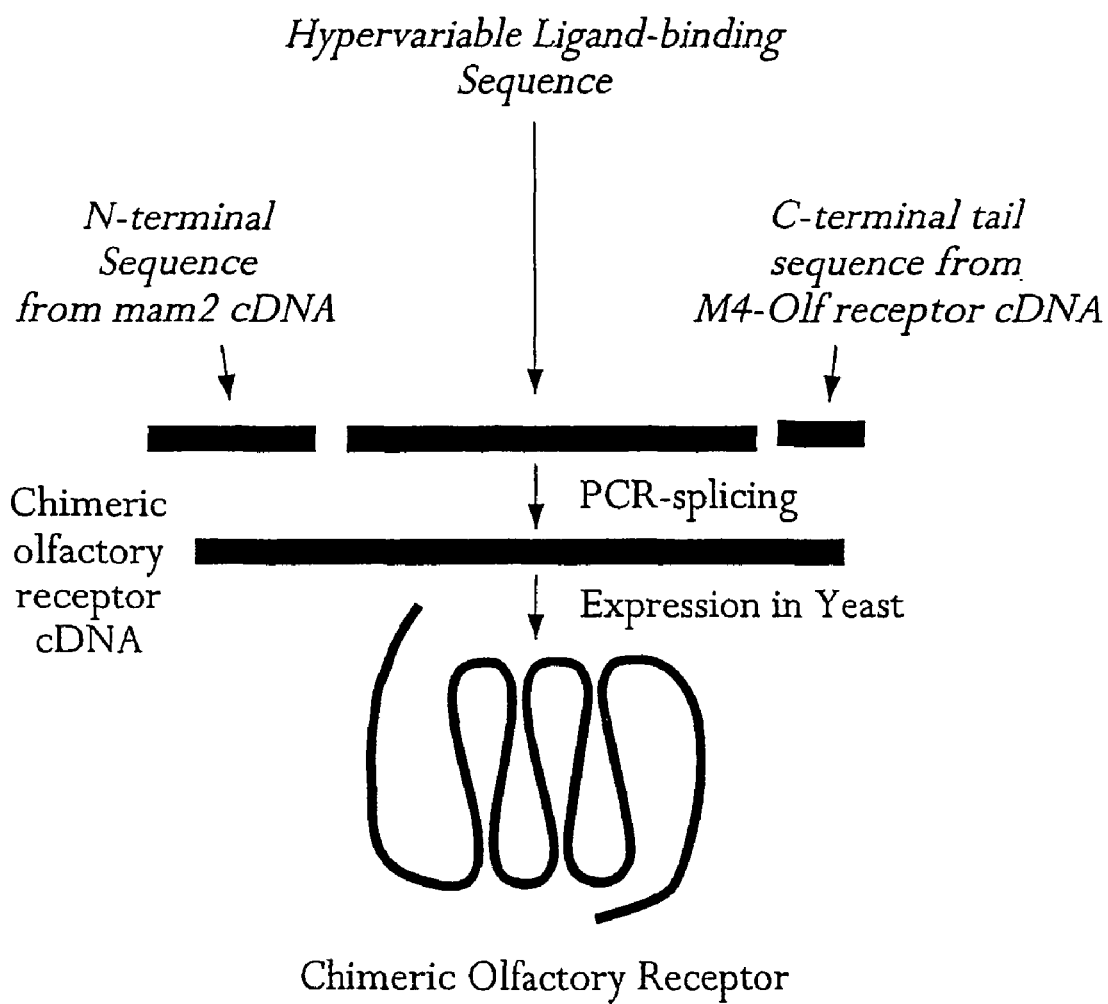
FIG. 3 shows the primary and secondary structure of a chimeric olfactory receptor.

Appropriate degenerate primers may be synthesized based on the consensus sequence of the species of interest. For example, the PCR reaction may be carried out on a cDNA library made from yeast, *C. elegans, Drosophila,* murine, canine, human or other olfactory or sensory cells. The PCR-products may be directly ligated into the basic expression vector cloning cassette, thereby generating vectors encoding chimeric receptors as shown in FIG. 3. Exemplary degenerate primers for PCR amplification of olfactory receptor hypervariable segments from the rat are given below in Table 1. Exemplary degenerate primers for PCR amplification of olfactory receptor hypervariable segments from the mouse are given below in Table 2.

TABLE 1

Exemplary degenerate primers for amplification of olfactory receptor hypervariable segments from the rat*

In the following primers, "I" is inosine.

Forward Primers

| | |
|---|---|
| 5'-AA(T/C)T(G/A)(G/C)ATI(C/A)TI(G/C)TIAA(T/C)(C/T)TIGCIGTIGCIGA-3' | (SEQ ID NO: 4) |
| 5'-AA(T/C)TA(T/C)TT(T/C)(C/A)TI(G/A)TIAA(T/C)CTIGCI(T/C)TIGCIGA-3' | (SEQ ID NO: 5) |
| 5'-AA(T/C)(T/C)(T/A)ITT(T/C)(A/C)TIATI(T/A)CICTIGCIT(G/C)IGCIGA-3' | (SEQ ID NO: 6) |
| 5'-(C/A)GITTI(C/T)TIATGTG(T/C)AA(C/T)CTI(T/A)(G/C)(C/T)TT(T/C)GCIGA-3' | (SEQ ID NO: 7) |
| 5'-ACIGTITA(T/C)ATIACICA(T/C)(C/T)TI(A/T)(C/G)IATIGCIGA-3' | (SEQ ID NO: 8) |

Reverse Primers

| | |
|---|---|
| 5'CTGI(C/T)(G/T)(G/A)TTCATIA(A/T)I(A/C)(C/A)(A/G)TAIA(T/C)IA(T/C)IGG(G/A)TT-3' | (SEQ ID NO: 9) |
| 5'-(G/T)(A/G)T(C/G)(G/A)TTIAG(A/G)CA(A/G)CA(A/G)TAIATIATIGG(G/A)TT-3' | (SEQ ID NO: 10) |
| 5'-TCIAT(G/A)TT(A/G)AAIGTIGT(A/G)TAIATIATIGG(G/A)TT-3' | (SEQ ID NO: 11) |
| 5'-GC(C/T)TTIGT(A/G)AAIATIGC(A/G)TAIAG(G/A)AAIGG(G/A)TT-3' | (SEQ ID NO: 12) |
| 5'-AA(A/G)TCIGG(G/A)(C/G)(T/A)ICGI(C/G)A(A/G)TAIAT(C/G)AIIGG(G/A)TT-3' | (SEQ ID NO: 13) |
| 5'-(G/C)(A/T)I(G/C)(A/T)ICCIAC(A/G)AA(A/G)AA(A/G)TAIAT(A/G)AAIGG(G/A)TT-3' | (SEQ ID NO: 14) |

*Adapted from Buck and Axel, supra.

Each of the five forward primers and each of the six reverse primers from Table 1 may be used simultaneously in PCR amplification reactions of reverse-transcribed rat olfactory epithelial RNA to obtain rat olfactory receptor hypervariable segment cDNAs. Appropriate PCR amplification conditions are known to those skilled in the art, for example as outlined in Buck and Axel, supra.

TABLE 2

Exemplary degenerate primers for amplification of olfactory receptor hypervariable segments from the mouse**

In the following primers, "P" is dP-CE phosphoramidite (6H,8H-3,4-dihydro pyrimido [4,5-c][1,2]

oxazin-7-one,8-[(5'-dimethoxytrityl-β-Ddeoxyribofuranosyl), 3'-[(2-cyanoethyl)-(N,N- diisopropyl)]-phosphoramidite). This compound is available from Glen Research (Sterling, VA).

TABLE 2-continued

Exemplary degenerate primers for amplification of olfactory receptor hypervariable segments from the mouse**

Forward Primer
5'-GGGGTCCGGAG(A/G)(C/G)T(A/G)A(A/G/T)AT(A/G/

P)A(A/G/P)(A/G/P)GG-3'

(SEQ ID NO: 15)

TABLE 2-continued

Exemplary degenerate primers for amplification of olfactory receptor hypervariable segments from the mouse**

Reverse Primer
5'-GGGGCTGCAGACACC(A/C/G/T)ATGTA(C/T)(C/T)T(A/C/

G/T)TT(C/T)(C/T)T-3'

(SEQ ID NO: 16)

**Adapted from Krautwurst et al., supra.

The primers in Table 2 may be used in PCR amplification reactions of reverse-transcribed mouse olfactory epithelial RNA to obtain mouse olfactory receptor hypervariable segment cDNAs. Appropriate PCR amplification conditions are known to those skilled in the art, for example as outlined in Krautwurst et al., supra.

Different variants of a given olfactory receptor protein may exist in nature. These variants may be allelic variations characterized by differences in the nucleotide sequences of the structural gene coding for the protein, or may involve differential splicing or post-translational modification. The skilled artisan can isolate or produce derivatives of an olfactory receptor protein hypervariable segment having single or multiple amino acid substitutions, deletions, additions, or replacements. These derivatives may include, inter alia: (a) derivatives in which one or more amino acid residues are substituted with conservative or non-conservative amino acids, (b) derivatives in which one or more amino acids are added to the protein, (c) derivatives in which one or more of the amino acids includes a substituent group, and (d) derivatives in which the protein is fused with another peptide. The techniques for obtaining these derivatives, including genetic (suppressions, deletions, mutations, etc.), chemical, and enzymatic techniques, are known to persons having ordinary skill in the art. See, for example, WO 97/35985, the disclosure of which is herein incorporated in its entirety, which describes methods of producing mutant olfactory receptor hypervariable segments.

Libraries of the chimeric olfactory receptor cDNAs may be generated by cloning the cDNAs into a basic expression vector, which may be propagated in an appropriate *E. coli* strain. Such libraries may be used to produce libraries of biosensors, by transfecting a yeast pre-biosensor strain containing an appropriate exogenous signaling pathway (e.g., WIF-1α, as described in Example 2).

The biosensors of the invention, either individually or in a library, may be tested to determine their ability to detect a given olfactant. The appropriate test for determining olfactant specificity depends on the signal reporter of the biosensor. For example, if the biosensor signal reporter comprises β-galactosidase, the biosensors may be grown in the presence of the olfactant and colony color developed by soft agar overlay using the chromogenic substrate X-gal. If the biosensor signal reporter comprises GFP, the biosensors may be grown in 96-well plates and the expression of GFP in response to the chemical agents of interest can be monitored.

Green fluorescent protein expressing yeast colonies or blue yeast colonies (i.e., those expressing olfactory receptor-driven β-galactosidase) representing biosensors of interest may be rescued from the primary plating, and subjected to multiple rounds of secondary validation assays to confirm sensitivity and specificity of activation for each biosensor. Confirmed positive clones may be subjected to DNA sequence analysis. Selected biosensors with defined olfactory ligand specificity may then be assembled into specific arrays for olfactant detection.

The methods for detecting biosensors of the present invention that can detect a given olfactant may be automated to provide convenient, real time, high volume methods of identifying biosensors with specific affinity for an olfactant. A test sample or environment may also be tested for the presence of an olfactant using one or more biosensors of known specificity. Preferably, automated methods are designed to detect the change in intracellular cAMP or $Ca^{++}$ in the biosensor, as will be apparent to those skilled in the art.

The invention thus provides a method of identifying biosensors which can detect a given olfactant, comprising the steps of providing at least one biosensor of the invention, wherein detection of the olfactant by the biosensor generates a detectable phenomenon from the signal reporter contacting the one or more biosensor with the olfactant; and observing whether the detectable phenomenon is produced from the signal reporter.

The invention further provides a method for detecting a selected olfactant in a sample, comprising the steps of providing one or more biosensors of the invention capable of detecting the olfactant, wherein detection of the olfactant by the biosensor generates a detectable phenomenon from the signal reporter; contacting the one or more biosensors with a sample suspected of containing the olfactant; and observing whether the detectable phenomenon is produced from the biosensor signal reporter. The sample to be tested may be liquid, gas, or a mixture of liquid and gas (e.g., air mixed with water vapor), or be susceptible to conversion into a liquid or gas (e.g., by volatilization, sublimation, melting, vaporization, or the like).

The detectable phenomenon may comprise fluorescence if the detectable molecule is a fluorescent indicator such as GFP. Other optical indicia that are suitable for real-time or long-term measurement of olfaction may also be used, as will be apparent to those skilled in the art.

Preferably the detectable phenomenon from the signal reporter is detected by an apparatus capable of detecting the phenomenon, for example an automated fluorescence plate reader. Generally an apparatus useful in the invention will comprise a measurement tool, such as a fluorescence measurement tool, for measuring the detectable phenomenon, means for controlling the measurement tool, such as a computer controller, and one or more biosensors of the invention (preferably comprising an array or biochip; see below). Measurement points may be over time, or among test and control biosensors.

A computer program product may control operation of the computer controller driving the measurement tool. A preferred computer program product comprises a computer readable storage medium having computer-readable program code means embodied in the medium. Hardware suitable for use in such automated apparatus will be apparent to those of skill in the art, and may include, automated sample handlers, printers and optical displays. The measurement tool may contain one or more photodetectors for measuring the fluorescence signals from samples where fluorescently detectable molecules are utilized. The measurement tool may also contain a computer-controlled stepper motor so that each biosensor can be arranged in an array and automatically and repeatedly positioned opposite a photodetector during the step of signal detection.

The measurement tool is preferably operatively coupled to a general purpose or application specific computer controller. The controller preferably comprises a computer program product for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application-specific integrated circuits for performing the above described functions and operations may be provided. Preferably, the stand-alone detection system is portable, and may be operated in the field under adverse conditions.

An array useful with the above-described apparatus may comprise a solid support carrying biosensors in fixed positions or cells. The appropriate pattern or distribution of biosensors in the array depends on the particular application, and can readily be determined by one of ordinary skill in the art.

The solid substrate onto which the biosensors are fixed or contained may comprise, for example, organic or inorganic substrates such as glass, polystyrenes, polyimides, silicon dioxide and silicon nitride. Other suitable substrates are known to those skilled in the art.

The arrays may be in the form of "biochips" comprising a set pattern of biosensors arranged on a substrate, optionally together with machine readable information encoded on the substrate. For example, the machine readable information may concern the location and type of biosensors on the chip. The machine readable information may be magnetic, optical (e.g., a bar code) or laser-based. The biochips may be in any convenient shape or size which allows it to be exposed to olfactants and read by a detector.

The present biosensors may also be arranged on or contained in a portable container, such as a vial or badge, that may be carried or worn by humans working an environment contaminated by noxious or toxic chemicals. The portable container may then be placed in an detection apparatus as described above to determine whether the badge (and therefore the bearer) has been exposed. In another embodiment, the portable container may comprise a built-in detection system, so that the bearer is immediately informed of an exposure.

It is understood that various combinations of the components for constructing the biosensors of the invention may be provided in kits. For example, one or more pre-biosensor cell lines and a basic expression vector as described above (i.e., an expression vector comprising a cloning cassette and sequences encoding defined olfactory receptor N- and C-terminal segments, as described above) may be provided. Optionally, the appropriate instructions and reagents for cloning olfactory receptor hypervariable segments into the basic expression vector, and for transfecting the master cell lines with these expression vectors, may be included in the kit.

Other kits may comprise the individual signaling pathway components for constructing a host master cell line as described above, for example in the form of plasmid vectors comprising nucleic acid sequences encoding the signaling pathway components, and a basic expression vector as described above. Again, the appropriate reagents and instructions for use may optionally be included. In a variation of this kit design, the kit may instead comprise one or more host master cell lines and one or more signal reporters for transfection into a master cell line to produce pre-biosensor cells. With such a kit, a user would be able to choose a signal reporter which suited his needs.

Further kits may comprise one or more fully constructed biosensors with or without defined olfactant specificities, for example in the form of a library to be screened. Again, the appropriate reagents and instructions for use may optionally be included.

The practice of invention is illustrated by the following non-limiting examples.

EXAMPLE 1

Construction of Yeast Master Strain WIF-1

The non-variable components of the cAMP signal transduction pathway consisting of the rat M4 Golf alpha subunit, the human G-protein β- and γ-subunits, and type III adenylyl cyclase (AC) were sequentially integrated into the yeast cell using two distinct yeast expression vectors derived from the yeast expression vector pESC. These vectors were:

| vector | component |
| --- | --- |
| 1. pESCtrp-Golf-cyc-DH5α | rat M4 Golf α-subunit; adenylate cyclase |
| 2. pESCura-β2γ5-DH5α | human G-protein β- and γ-subunits |

Vectors 1 and 2 were deposited on Feb. 1, 2001 with the patent culture collection of the National Center for Agricultural Utilization Research, Agricultural Research Service, U.S. Department of Agriculture (NRRL), 1815 North University Street, Peoria, Ill. 61604 U.S.A., in accordance with the Budapest Treaty, and have been assigned accession nos. NRRL B-30412 and NRRL B-30414, respectively. Master yeast strain WIF-1 was deposited on Feb. 7, 2001 with the NRRL in accordance with the Budapest Treaty; accession no. NRRL Y-30415.

1.1—Construction of the Yeast Expression Vectors pESCtrp-Golf-cyc-DH5α—Rat M4 Golf α-subunit (Gαolf) was cloned from rat olfactory epithelial lamellae total RNA using RT-PCR. Reverse transcription of the mRNA into cDNA was carried out using the Ready-To-Go™ T-Primed First-Strand Kit manufactured by Amersham Pharmacia Biotech Inc USA, using the manufacturer's protocol. The following primers were used for the subsequent PCR of Gαolf:

```
Forward (sense):
5'-AGCCAGCAGGCATGGGGTGTTTGG-3'    (SEQ ID NO: 17)

Reverse (antisense):
5'-TCACAAGAGTTCGTACTGCTTGAG-3'    (SEQ ID NO: 18)
```

The PCR cycling protocol was 1×2 min at 94° C.; 30×1 min each at (94° C., 60° C., 72° C.); 1×10 min. at 72° C. using pfuTURBO DNA polymerase.

The PCR product containing the Gαolf sequence and the 5'-upstream Kozak sequence was inserted into sub-cloning vector pCR2.1 (Invitrogen). After checking the orientation of the inserted Gαolf cDNA by restriction and sequence analyses, the insert in the right orientation was excised from pCR2.1 vector by Not I and Sac I. The excised and gel purified Not I-Sac I Gαolf insert was cloned into yeast expression vector pESC-trp (Stratagene) digested with Not I and Sac I to produce pESCtrp-Golf. The presence of the Gαolf sequence in pESCtrp-Golf was verified by DNA sequencing. pESCtrp-Golf was propagated in *E. coli* DH5α, and the plasmid was purified for the subsequent insertion of the cDNA encoding adenylyl cyclase.

The cloning vector pBSK KS containing olfactory adenylyl cyclase (AC) type III (obtained from Dr. Randall R. Reed, Johns Hopkins) was propagated in *E. coli* DH5α and the plasmid was purified by standard techniques. The cDNA sequence encoding AC was excised from pBSK KS by digestion with Apa I and Nhe I. The Apa I-Nhe I AC fragment was cloned into pESCtrp-Golf that had been digested with Apa I and Spe I to produce pESCtrp-Golf-cyc-DH5α. pESCtrp-Golf-cyc-DH5α was propagated in *E. coli* DH5α.

pESCura-β2γ5-DH5α—The cDNA encoding human G-protein beta subunit β2 was excised from the cloning vector pSP73 (kindly provided by Dr. Shoji Osawa, University of North Carolina at Chapel Hill) using restriction enzymes Hind III-EcoRI, and ligated into the Sal I-Xho I linearized yeast expression vector pESC-ura The cDNA sequence for the human G-protein beta subunit β2 is given in SEQ ID NO: 32, and the predicted amino acid sequence is given in SEQ ID NO: 33. See also GenBank record accession no. X04526, the disclosure of which is herein incorporated by reference. The orientation of the β2-insert was confirmed by restriction and sequence analyses. In the resultant vector, named pESCura-β2, the cDNA for human G-protein gamma subunit γ5 was introduced as follows: The cDNA insert encoding human γ5 was excised from pBluescript SK (kind gift from Dr. Janet Robishaw, Geisinger Clinic, Danville, Pa.) using the restriction enzymes Pvu I and Eco RI. The human G-protein γ5 cDNA sequence is given in SEQ ID NO: 34, and the predicted amino acid sequence is given in SEQ ID NO: 35. See also GenBank record accession no. AF188178, the disclosure of which is herein incorporated by reference. The Pvu I-Eco RI cDNA fragment containing human γ5 was cloned into pESCura-β2 digested with Eco RI-Pac I sites by blunt-end ligation to produce pESCura-β2γ5-DH5α, and propagated in DH5α.

1.2—Transfection of *S. cerevisiae* with the Yeast Expression Vectors to Form Yeast Host Master Cell WIF-1

Yeast cells competent for transfection were prepared as follows: Several colonies of the YPH 501 strain of the yeast *S. cerevisiae*, which is an auxotrophic mutant for the amino acids Trp, Leu, Ura, and His, were inoculated into 50 ml of YPD medium (1% yeast extract, 2% Bacto peptone, 2% dextrose, and 0.0075% adenine-hemisulfate in 1 liter of distilled water), and incubated at 30° C. for 16-18 hr with shaking at 200 rpm to obtain stationary phase cultures ($OD_{600}$ greater than 1.5). Thirty ml of the stationary culture was transferred to 300 ml of fresh YPD medium, and was regrown at 30° C. for 3 hr with shaking at 200 rpm until the $OD_{600}$ reached 0.4-0.6. Cells competent for transfection were collected by centrifugation (1000×g for 5 min at room temperature) and the cell pellet was washed by resuspension in 25-50 ml of sterile TE (Tris 10 mM, pH 7.5 and 1 mM EDTA) followed by centrifugation. The competent cells were then resuspended in 1.5 ml of freshly prepared sterile TE/LiAc solution (100 mM lithium acetate in TE).

Yeast expression vectors pESCtrp-Golf-cyc (100 ng) and pESCura-β2γ5 (100 ng) and 0.1 mg of carrier DNA (herring testes DNA) in a total volume of 0.015 ml were placed in a 1.5 ml tube into which 0.1 ml of competent cells were added and mixed thoroughly. In to this mixture, 0.6 ml of sterile PEG/LiAc solution (40% PEG-4000 in TE/LiAc solution) was added and mixed by vortexing for 10 sec. Following a brief incubation for 30 min at 30° C. in a shaking incubator, 0.07 ml of DMSO was added and the tube contents were gently mixed. The tubes were then subjected to heat-shock (42° C.) for 15 min, after which each tube was chilled in an ice-water bath for 2 min. The transfected cells were collected by centrifugation (14000 g for 5 sec at room temperature) and the cell pellet was resuspended in 0.5 ml of sterile TE buffer.

An aliquot (0.1-0.2 ml) of the cells were plated onto a 100-mm petri dish containing SD trp, ura amino acid drop-out medium (6.7 g yeast nitrogen base without amino acids, 20 g glucose, 20 g Agar and 1 Liter water containing L-Isoleucine, 30 mg/l; L-Valine, 150 mg/l; L-Adenine Hemisulfate, 20 mg/l; L-Arginine, 20 mg/l; L-histidine, 20mg/l; L-methionine, 20 mg/l; L-tyrosine, 30 mg/l, L-threonine 200 mg/l; L-Phenylalanine, 50 mg/l, L-lysine, 30 mg/l; and L-leucine, 100 mg/l, but does not contain L-Tryptophan and L-Uracil). Thus, the SD trp, ura amino acid drop-out medium selects for transfected cells harboring both pESCtrp-Golf-cyc and pESCura-β2γ5 expression vectors.

The petri-dishes were incubated at 30° C. for 2-4 days or until colonies appeared. The larger colonies were picked and grown on fresh selective SD trp, ura amino acid drop-out medium (agar dishes as well as liquid medium). A yeast host master cell containing pESCtrp-Golf-cyc and pESCura-β2γ5 expression vectors was isolated and named WIF-1. This host master cell was stored as glycerol stocks (25%) at −80° C.

EXAMPLE 2

Construction of Yeast Reporter Strain WIF-1α

The WIF-1 host master cell described above can be transfected with signal reporters of different types to form pre-biosensor cells. Transfection vectors comprising three separate signal reporters (for the construction of three separate pre-biosensor cells) have been constructed. These vectors were:

| vector | component |
| --- | --- |
| 3. pESChis-creb-cregfp-DH5α | CREB; CRE-driven GFP |
| 4. pESChis-creb-cregal-DH5α | CREB; CRE-driven beta galactosidase |
| 5. pESChis-ONGC-aeq-DH5α | $Ca^{++}$ channel; Apoaequorin |

Vector 3 (pESChis-creb-cregfp-DH5α) was deposited on Feb. 1, 2001 with the patent culture collection of the National Center for Agricultural Utilization Research, Agricultural Research Service, U.S. Department of Agriculture (NRRL), 1815 North University Street, Peoria, Ill. 61604 U.S.A., in accordance with the Budapest Treaty, and has been assigned accession no. NRRL B-30413.

2.1—Construction of the Yeast Expression Reporter Vector pESChis-creb-cregfp-DH5α pESChis-creb-cregfp-DH5α: This construct was made using the yeast expression vector, pESC-HIS. The CRE-driven GFP was inserted in place of the pESC-HIS GAL1 promoter; to this end, the GAL1 promoter of pESC-HIS was excised by digestion with Bam HI and Age I. pESC-His was religated to form the circularized pESCDG1-HIS vector.

The cDNA encoding human CREB was excised from pCMV-CREB vector (Clontech, Palo Alto, Calif.) by digestion with Eco RI and Xba I, and ligated into pESCDG1-HIS linearized by digestion with Eco R I-Spe I. The resultant vector was named pESCDG1-His-CREB.

A modified cDNA encoding GFP under the control of human CRE promoter was obtained from pCRE-d2EGFP vector by PCR amplification. The PCR primers were designed so that the resulting PCR product lacked the destabilizing PEST-sequence (introduced into pCRE-d2EGFP by Clontech to monitor dynamic changes in GFP-expression because it enhances degradation of the protein) and contained a new stop-codon. The PCR primers were:

Forward (sense) primer:
    5'-TAGGTACCGAGCTCTTACGCGTGCTAGCGCA-3'

(SEQ ID NO: 19)

Reverse (antisense) primer:
    5'-GCTCTAGATTACTTGTACAGCTCGTCCATGCCGAG-3'

(SEQ ID NO: 20)

The PCR cycling protocol was 1×2 min. at 94° C.; 30×1 min. each at (94° C., 60° C., 72° C.); 1×10 min. at 72° C. using pfuTURBO DNA polymerase. The PCR product containing the CRE and GFP cDNA in tandem was cloned into pESCDG1-His-CREB vector by blunt-end ligation into the Sma I site, after the cut-ends of the vector had been filled in. The orientation and the sequence of the CRE-GFP insert were verified by DNA sequencing. The vector was named pESChis-creb-cregfp, and propagated in DH5α.

2.2—Transfection of WIF-1 with pESChis-creb-cregfp-DH5α to Form Pre-biosensor WIF-1α

Several colonies of WIF-1 host master cell (described above) were grown 50 ml of YPD medium (see above) and incubated at 30° C. for 16-18 hrs with shaking at 200 rpm to obtain stationary phase cultures ($OD_{600}$ greater that 1.5). Thirty ml of the stationary cultures were transferred to 300 ml of YPD medium and regrown at 30° C. for 3 hr with shaking (200 rpm) until the $OD_{600}$ reached 0.4-0.6. The host master cells were collected by centrifugation (1000×g for 5 min at room temperature) and the cell pellet was washed by resuspension in 25-50 ml of sterile TE followed by centrifugation. The host master cells were resuspended in 1.5 ml of freshly prepared sterile TE/LiAc solution (see above) in preparation for transfection.

Yeast expression vector pESChis-creb-cregfp (100 ng) and 0.1 mg of carrier DNA (herring testes DNA) in a total volume of 0.015 ml was placed in a 1.5 ml tube into which 0.1 ml of WIF-1 host master cells had been added, and mixed thoroughly. Into this mixture, 0.6 ml of sterile PEG/LiAc solution (see above) was added and mixed by vortexing for 10 sec. Following a brief incubation for 30 min at 30° C. in a shaking incubator, 0.07 ml of DMSO was added and the tube contents gently mixed. The tubes were then subjected to heat-shock (42° C.) for 15 min, after which the tube was chilled in an ice-water bath for 2 min.

The transfected WIF-1 cells were collected by centrifugation (14000 g for 5 sec at room temperature) and the cell pellet was resuspended in 0.5 ml of sterile TE buffer. An aliquot (0.1-0.2 ml) of the cells were plated onto a 100-mm petri-dish containing SD his, trp, ura drop-out amino acid medium (6.7 g yeast nitrogen base without amino acids, 20 g glucose, 20 g Agar and 1 Liter water containing L-Isoleucine, 30 mg/l; L-Valine, 150 mg/l; L-Adenine Hemisulfate, 20 mg/l; L-Arginine, 20 mg/l; L-methionine, 20 mg/l ; L-tyrosine, 30 mg/l, L-threonine 200 mg/l; L-Phenylalanine, 50 mg/l, and L-lysine, 30 mg/l, but not L-leucine, L-Histidine, L-Tryptophan and L-Uracil). Thus, the SD his, trp, ura drop-out amino acid medium selects for transfected WIF-1 cells (i.e., pre-biosensor cells) that harbor pESChis-creb-cregfp-DH5α in addition to pESCtrp-Golf-cyc-DH5α and pESCura-β2γ5-DH5α expression vectors.

The petri-dishes were incubated at 30° C. for 2-4 days or until colonies of pre-biosensor cells appeared. The larger colonies were picked and grown on fresh selective SD his, trp, ura drop-out amino acid medium (on agar dishes as well as in medium liquid medium). A pre-biosensor transfected with pESChis-creb-cregfp-DH5α in addition to pESCtrp-Golf-cyc-DH5α and pESCura-β2γ5-DH5α expression vectors was isolated and named WIF-1α. WIF-1α was stored as glycerol stocks (25%) at −80° C.

2.3—Transfection of WIF-1 with pESChis-creb-cregal-DH5α and pESChis-ONGC-aeq-DH5α

Yeast host master cell WIF-1 is transfected with either pESChis-creb-cregal-DH5α or pESChis-ONGC-aeq-DH5α as described above for pESChis-creb-cregfp-DH5α to produce prebiosensors WIF-1-gal and WIF-1aeq.

EXAMPLE 3

Transfection of Pre-Biosensor WIF-1α with pESCleu-RI7-DH5α to Form Biosensor WIF-1α-RI7

Rat olfactory receptor R17, which is responsive to octaldehyde, was cloned by RT-PCR methods using mRNA isolated from rat olfactory epithelium. This receptor was cloned into modified yeast pESC expression vector pESCleu-RI7-DH5α, which was transfected into the olfactory pre-biosensor WIF-1α to produce biosensor WIF-1α-R17.

3.1—Construction of pESCleu-RI7-DH5α—The rat olfactory receptor R17 receptor was cloned from rat olfactory epithelial lamellae total RNA using RT-PCR. Reverse transcription of the mRNA into DNA was carried out using the Ready-To-Go™ T-Primed First-Strand Kit manufactured by Amersham Pharmacia Biotech Inc., USA using the manufacturer's protocol. The following primers were used for the subsequent amplification of the RI7 receptor:

```
Forward (sense) primer:
ATGGAGCGAAGGAACCACAGTGGG      (SEQ ID NO: 21)

Reverse (antisense) primer:
CTAACCAATTTTGCTGCCTTTGTTGG    (SEQ ID NO: 22)
```

The PCR cycling protocol was 1×2 min at 94° C., 30×(30 sec at 94° C., 30 sec at 55° C., 1 min at 72° C.), and 1×15 min at 72 ° C. The PCR product (984 bp) was gel-purified and cloned into the cloning vector pCR2.1 (Invitrogen). After verifying the insert by sequencing, the insert containing RI7 was excised out of pCR2.1 vector with Not I and Sac I restriction enzymes. The insert was gel-purified and ligated to the Not I-Sac I linearized pESC-LEU vector, and the resultant vector was verified by sequence analysis. This vector was named pESCleu-RI7-DH5α and propagated in *E. coli* DH5α.

3.2—Transfection of WIF-1α with pESCleu-RI7-DH5α—To obtain cells competent for transfection, several colonies of WIF-1α strain of yeast were grown 50 ml of YPD medium and incubated at 30° C. for 16-18 hrs. with shaking at 200 rpm to obtain stationary phase cultures ($OD_{600}$ greater that 1.5). Thirty ml of the stationary culture was transferred to 300 ml of YPD medium and regrown at 30° C. for 3 hr with shaking (200 rpm) until the $OD_{600}$ reached 0.4-0.6. The cells were collected by centrifugation (1000×g for 5 min at room temperature) and the cell pellet was washed with 25-50 ml of sterile TE by centrifugation.

The competent cells were resuspended in 1.5 ml of freshly prepared sterile TE/LiAc solution (see above). Yeast expression vector pESCleu-RI7-DH5α (100 ng) and 0.1 mg of carrier DNA (herring testes DNA) in a total volume of 0.015 ml was placed in a 1.5 ml tube into which 0.1 ml of competent cells were added and mixed thoroughly. 0.6 ml of sterile PEG/LiAc solution was added and the tube contents mixed by vortexing for 10 sec. Following a brief incubation for 30 min at 30° C. in a shaking incubator, 0.07 ml of DMSO was added and gently mixed. The tubes were then subjected to heat-shock (42° C.) for 15 minutes, after which the tubes were chilled in an ice-water bath for 2 min. The cells were collected by centrifugation (14000 g for 5 sec at room temperature) and the cell pellet was resuspended in 0.5 ml of sterile TE buffer. An aliquot (0.1-0.2 ml) of the cells was plated onto a 100-mm petri-dish containing SD leu, his, trp, ura drop-out amino acid medium (6.7 g yeast nitrogen base without amino acids, 20 g glucose, 20 g Agar and 1 Liter water containing L-Isoleucine, 30 mg/l; L-Valine, 150 mg/l; L-Adenine Hemisulfate, 20 mg/l; L-Arginine, 20 mg/l; L-methionine, 20 mg/l; L-tyrosine, 30 mg/l, L-threonine 200 mg/l; L-Phenylalanine, 50 mg/l, and L-lysine, 30 mg/l, but not L-Leucine, L-Histidine, L-Tryptophan and L-Uracil). This medium selects for yeast cells that harbor pESCleu-RI7-DH5α in addition to pESChis-creb-cregfp-DH5α, pESCtrp-Golf-cyc-DH5α and pESCura-β2γ5-DH5α expression vectors.

The petri-dishes were incubated at 30° C. for 24 days or until colonies appeared. The larger colonies were picked and grown on fresh selective SD leu, his, trp, ura drop-out amino acid medium (agar dishes as well as in liquid medium). A yeast biosensor expressing pESChis-creb-cregfp-DH5α in addition to pESCtrp-Golf-cy-DH5α and pESCura-β2γ5-DH5α expression vectors was thus isolated, and named WIF-1α-R17. WIF-1α-R17 was stored as glycerol stocks (25%) at −80° C.

EXAMPLE 4

Construction of Basic Expression Vector pESCleu-RX-DH5α

Yeast basic expression vector pESCleu-RX-DH5α, containing N- and C-terminal segments from the rat RI7 olfactory receptor flanking a cloning cassette, was constructed from pESCleu-RI7-DH5α as described below. This basic expression vector can receive any olfactory receptor hypervariable segment into the cloning cassette and be transfected into a yeast pre-biosensor cell, where it will express a chimeric olfactory receptor.

A cDNA fragment encoding the N-terminal 61 amino acids of RI7 plus unique Bgl II and Pst I cloning sites was generated by PCR from pESCleu-RI7-DH5α. The primers used to generate the fragment were a 5'-sense primer that anneals to the segment spanning the Dra III site (nucleotide position 2698 of the pESCleu vector back-bone) of pESCleu-RI7 (the "5' Dra III primer"), and a reverse primer (the "NT-RX" primer) that can anneal to nucleotides 183-163 of the RI7-cDNA.

```
5' Dra III primer:
5'-AGGGCGATGGCCCACTACGTGAACCATCACCCT-3'

(SEQ ID NO: 23)

NT-RX primer:
5'-AGAGAGAGATCTGCAGATACATGGGTTTGTGGAGGGT-3'

(SEQ ID NO: 24)
```

Similarly, a cDNA fragment encoding the C-terminal 35 amino acids of RI7 plus unique Bgl II and Spe I cloning sites was generated by PCR amplification from pESCleu-RI7-DH5α using the following primers: a 5'-sense primer (the "CT-RX" primer) that can anneal to nucleotides 881-898 of the RI7 cDNA, and a reverse primer that can anneal to the segment spanning the Hind III site (nucleotide position 4140 of the pESCleu vector back-bone) of pESCleu-RI7 (the "3' Hind III" primer).

```
CT-RX primer:
5'-AGAGAGAGATCTACTAGTATCTACTGCTTGCGCAAC-3'

(SEQ ID NO: 25)

3' Hind III primer:
5'-CTAGCCGCGGTACCAAGCTTACTCGAGGTCTTC-3'

(SEQ ID NO: 26)
```

The PCR-generated, N-terminus encoding cDNA was cut with Dra III and Bgl II, whereas the C-terminus encoding fragment was cut with Bgl II and Hind III. The fragments were ligated to each other at the Bgl II sticky ends to generate a Dra III-Hind III fragment. This fragment contained nucleotides 1-183 of the RI7 cDNA (that encode the N-terminal 61 amino acids of RI7) and nucleotides 881-984 of the RI7 cDNA (that encode the C-terminal 35 amino acids of RI7) flanking a Pst I, Bgl II, and Spe I cloning cassette.

The Dra III-Hind III fragment was cloned into pESC-LEU vector digested with Dra III-Hind III to produce pESCleu-RX-DH5α. The sequence of the vector was verified by sequence analysis, and the construct was propagated in E. coli DH5α.

pESCleu-RX-DH5α was deposited on Feb. 1, 2001 with the patent culture collection of the National Center for Agricultural Utilization Research, Agricultural Research Service, U.S. Department of Agriculture (NRRL), 1815 North University Street, Peoria, Ill. 61604 U.S.A., in accordance with the Budapest Treaty, and has been assigned accession no. NRRL B-30411.

EXAMPLE 5

Detection of Chemical Agents by WIF-1α-RI7

WIF-1α-R17 was able to detect different concentrations of octaldehyde, as revealed by the expression of GFP seen with a fluorescence reader. Using different alcohols and aldehydes, the specificity of WIF-1α-R17 for octaldehyde was also demonstrated.

Pre-biosensor WIF-1α (R17 olfactory receptor negative; see Example 2) and biosensor WIF-1α-R17 (R17 olfactory receptor positive; see Example 3) were grown in SD leu, his, trp, ura amino acid drop-out media (see Example 3.3, above) for 8 hrs. $3 \times 10^8$ cells were reinoculated in 100 ml of SD dropout media for 16 hrs to induce the expression of the signaling and signal reporter components (Gαolf, β2, γ5, adenylate cyclase, CREB) as well as the RI7 olfactory receptor. At the end of 16 hours, the cells were seeded into 48- or 96-well plates ($7 \times 10^7$ cells/well) and used to determine the sensitivity and specificity of the WIF-1α-R17 biosensor.

Figure 4A:
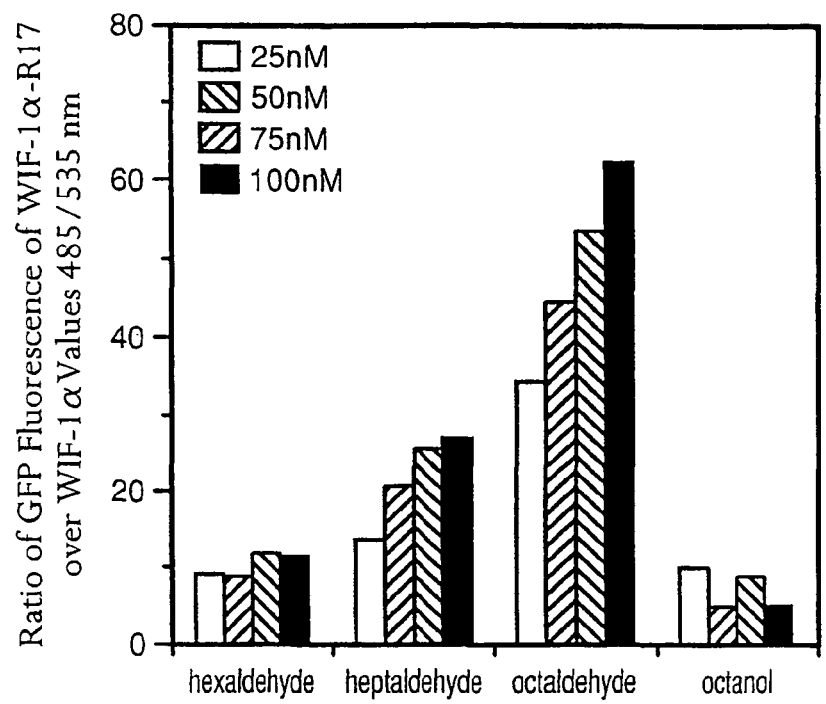
FIG. 4A shows the sensitivity of biosensor WIF-1α-RI7 by plotting the ratio of WIF-1α-RI7 GFP fluorescence values over pre-biosensor WIF-1α (control) GFP fluorescence values for different olfactants at varying concentrations (25, 50, 75, and 100 nM).

5.1—Sensitivity of WIF-1α-R17 for Different Olfactants—The yeast pre-biosensor WIF-1α and biosensor WIF-la-R17 were exposed to each of four different olfactants (hexaldehyde, heptaldehyde, octaldehyde and octanol) at varying concentrations (25, 50, 75, and 100 nM) for 3 hours, and the GFP fluorescence was measured in a Perkin-Elmer BioAssay 7000 plus reader using 485 nm for excitation and 535 nm for emission. The ratio of WIF-1α-R17 GFP fluorescence values over WIF-1α (control) GFP fluorescence values for each olfactant at each concentration are given in FIG. 4A. As expected, biosensor WIF-1α-R17 shows greater sensitivity for octaldehyde at all concentrations tested.

Figure 4B:
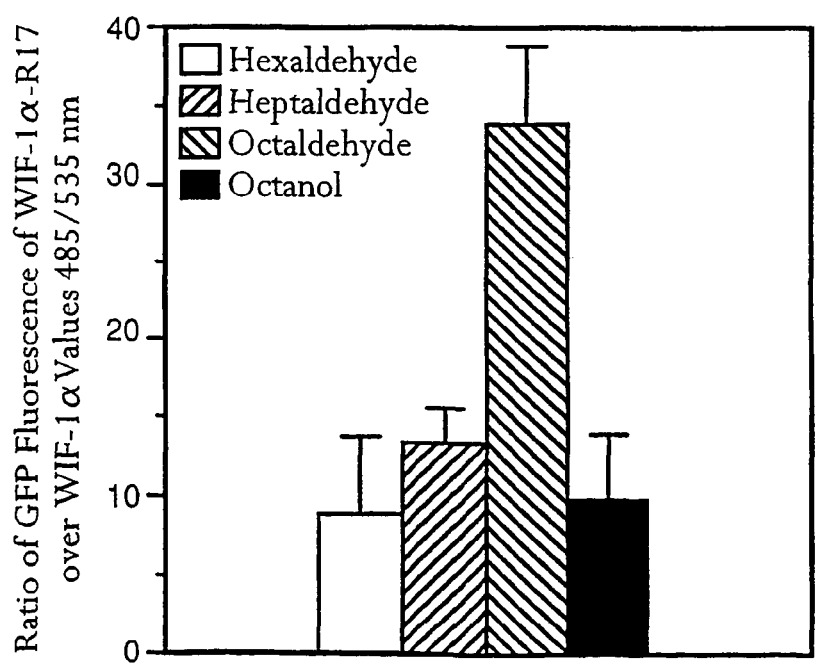
FIG. 4B shows the specificity of biosensor WIF-1α-RI7 for different olfactants by plotting the ratio of WIF-1α-RI7 GFP fluorescence values over pre-biosensor WIF-1α (control) GFP fluorescence values for different olfactants at a single concentration (25 nM).

5.2—Specificity of WIF-1α-R17 for Different Olfactants—The yeast pre-biosensor WIF-1α and biosensor WIF-1α-R17 were exposed to a single concentration (25 nM) of four different olfactants (hexaldehyde, heptaldehyde, octaldehyde and octanol) for 3 hours, and GFP fluorescence was measured in a Perkin-Elmer BioAssay 7000 plus reader using 485 nm for excitation and 535 nm for emission. The ratios of WIF-1α-R17 GFP fluorescence values over WIF-1α (control) GFP fluorescence values for each olfactant are given in FIG. 4B. As expected, biosensor WIF-1α-R17 exhibited greater specificity for octaldehyde.

EXAMPLE 6

Expression Analyses of Mammalian Olfactory Signaling Components in WIF-1α-RI7

The expression of mammalian olfactory signaling components was confirmed in yeast biosensor WIF-1α-RI7 as follows.

Figure 5A:
FIG. 5A is a photograph of a 1% agarose gel showing detection of a 984 bp RI7 PCR fragment from control and WIF-1α cells.

Detection of RI7 Olfactory Receptor RNA—Total RNA from WIF-1α-RI7 and untransfected yeast control cells was extracted using the QIAGEN RnaEasy kit according to the manufacturer's instructions. The RNA was reverse-transcribed using the Superscript first strand synthesis system (GIBCO/Invitrogen), and was subjected to PCR amplification with the RI7 primers and conditions described in Example 3.1 above. The PCR reaction is expected to amplify a 984 bp RI7 fragment. An aliquot of the PCR reaction was electrophoresed on a 1% agarose gel. FIG. 5A shows that the expected 984 bp RI7 fragment was present in WIF-1α-RI7 cells, but not in control cells.

Figure 5B:
FIG. 5B is Western blot showing detection of CREBP and Gαolf protein in control and WIF-1α cells.
Figure 5B:
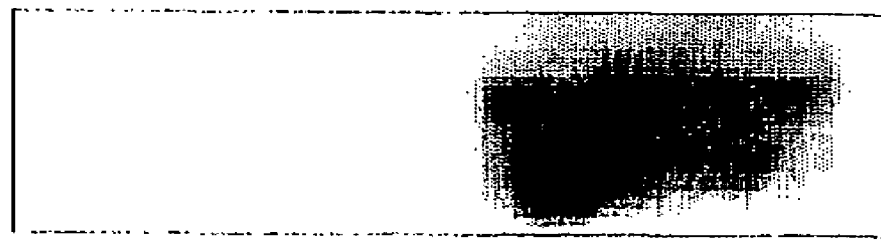

Detection of CREBP and Gαolf Proteins—Total protein was extracted from WIF-1-α-RI7 and untransfected yeast control cells using the "bead-bashing" technique described in Dunn B and Wobbe C R (1993), "Preparation of protein extracts from yeast," in *Current Protocols in Molecular Biology*, (Ausubel F M et al., eds.), John Wiley & Sons, Inc., New York, pp. 13.13.1-13.13.9, the disclosure of which is herein incorporated by reference. The protein extracts were subjected to standard Western blot analysis using antibodies specific for CREBP (New England Biolabs; Cat. #9192) or the Gαolf protein (Santacruz, Calif.; Cat. #SC-385). FIG. 5B shows that both CREBP and Gαolf proteins were present in WIF-1α-RI7, but not in the control cells.

EXAMPLE 7

Membrane Localization of Gαolf in WIF-1α-RI7

To verify the membrane localization of Gαolf in the WIF-1α-RI7 biosensor, WIF-1α-RI7 cells expressing Gαolf protein were permeablized using 20 units of lyticase (Sigma, Mo.) for 30 min at 30° C. Permeablized cells were collected by centrifugation, and incubated with anti-Gαolf antibody (Santacruz, Calif.; Cat. # SC-385) at 1:200 dilution for 1 hr., followed by a further 1 hr. incubation with anti-immunoglobulin antibodies labeled with Texas-red fluorophore (Molecular Probes, Oreg.; Cat # T-2767) at 1:500 dilution. Ten microliters of these cells were then mounted on a slide and analyzed with a laser confocal microscope (Olympus). Red fluorescence representing the Gαolf protein was observed in the WIF-1α-RI7 cells and was localized to the cell membrane. WIF-1α-RI7 cells stained either with primary or secondary antibody alone were used as controls, and no significant red fluorescence was seen in these cells.

EXAMPLE 8

Detection of GFP Response in WIF-1α-RI7 Cells

WIF-1α-RI7 cells were exposed to 100 nmoles of hexaldehyde (6-CHO), heptaldehyde (7-CHO) or octaldehyde (8-CHO). Control cells were not exposed to any olfactant. At 3 hrs. post-exposure, 10 microliters of cells were removed from each treatment group and the control group, and mounted separately on slides. GFP expression in the presence of the olfactant was detected in each sample by laser confocal microscopy, and the results are shown in FIGS. 6A-6D.

FIG. 6A shows the background expression of GFP in the absence of olfactant. Exposure of the cells to hexaldehyde produced GFP expression essentially equal to background (see FIG. 6B). FIG. 6C shows an increased GFP expression in cells exposed to heptaldehyde with respect to the control and hexaldehyde-exposed cells. FIG. 6D shows an increase in GFP expression in cells exposed to octaldehyde with respect to heptaldehyde-exposed cells. These results show that WIF-1α-RI7 cells specifically detect octaldehyde, with some detection of heptaldehyde, the closest homolog to octaldehyde. There is no detection of hexaldehyde, a homolog only two carbons removed from octaldehyde, by the WIF-1α-RI7 cells.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

---

What is claimed is:

1. A biosensor comprising a yeast expressing the following elements:
   (a) at least one olfactory receptor protein for binding olfactant;
   (b) at least one exogenous signaling pathway coupled to the at least one olfactory receptor for transducing a signal produced by the at least one olfactory receptor upon olfactant binding; and
   (c) at least one signal reporter coupled to the signaling pathway for producing a detectable phenomenon upon transduction of the olfactant binding signal by the signaling pathway,
   wherein the at least one olfactory receptor protein comprises:
   (i) an olfactory receptor hypervariable segment which contains at least one olfactant binding site;
   (ii) a processing/transport segment which directs the processing and transport of the receptor in the yeast, wherein the processing/transport segment is located N-terminal to the olfactory receptor hypervariable segment; and (iii) a coupling segment which couples the receptor to the at least one exogenous signaling pathway in the yeast, wherein the coupling segment is located C-terminal to the olfactory receptor hypervariable segment.

2. The biosensor of claim 1, wherein the processing/transport segment comprises the first 60 amino acids of the yeast mam2 protein, and the coupling segment comprises the last 35 amino acids of the rat RI7 receptor.

3. The biosensor of claim 1, wherein the processing/transport segment comprises the first 61 amino acids of the rat RI7 olfactory receptor, and the coupling segment comprises the last 35 amino acids of the rat RI7 receptor.

4. The biosensor of claim 1, wherein the at least one signaling pathway comprises a G-protein and an adenylate cyclase.

5. The biosensor of claim 1, wherein the at least one signal reporter is responsive to intracellular cAMP or $Ca^{++}$ levels.

6. The biosensor of claim 5, wherein the at least one signal reporter is selected from the group consisting of a cyclic AMP-responsive GFP expression system, a cyclic AMP-responsive β-galactosidase expression system, a $Ca^{++}$-responsive luminescence reporter system, a fluorescent cytosolic $Ca^{++}$ indicator, and the electrophysiological detection of $Ca^{++}$ influx.

7. The biosensor of claim 5, wherein the at least one signal reporter comprises GFP.

8. The biosensor of claim 1, wherein the at least one signaling pathway comprises an olfactory receptor G-protein, type III adenylyl cyclase, and the at least one signal reporter comprises CREB and CRE-driven GFP.

9. A method of identifying biosensors which can detect a selected olfactant, comprising the steps of:
(1) providing at least one biosensor of claim 1;
(2) contacting the at least one biosensor with the selected olfactant; and
(3) observing whether said detectable phenomenon is produced from the signal reporter of said biosensor.

10. The method of claim 9, wherein the signal is detected by an apparatus comprising a measurement tool for detecting the detectable phenomenon and a computer controller for controlling operation of the measurement tool.

11. The method of claim 10, wherein the at least one biosensor is located in a fixed position on an array comprising a solid support.

12. The method of claim 10, wherein the at least one biosensor is located in a set pattern on a biochip comprising a solid substrate, optionally together with machine readable information encoded on the substrate identifying the location and type of the at least one biosensor.

13. The method of claim 10, wherein the apparatus is portable.

14. An apparatus capable of detecting the detectable phenomenon produced by a biosensor of claim 1, comprising a measurement tool for measuring the detectable phenomenon, a computer controller for controlling the measurement tool and at least one said biosensor.

15. The apparatus of claim 14, wherein the at least one biosensor is located in a fixed position on an array comprising a solid support.

16. The apparatus of claim 14, wherein the at least one biosensor is located in a set pattern on a biochip comprising a solid substrate, optionally together with machine readable information encoded on the substrate identifying the location and type of the at least one biosensor.

17. A method for detecting a selected olfactant in a sample, comprising:
(1) providing at least one biosensor of claim 1 capable of detecting the olfactant, wherein detection of the olfactant generates a detectable phenomenon from the signal reporter of said biosensor;
(2) contacting said at least one biosensor with a sample suspected of containing the olfactant; and
(3) observing whether said detectable phenomenon is produced from the signal reporter.

18. The method of claim 17, wherein said detectable phenomenon comprises fluorescence.

19. The method of claim 17, wherein the detectable phenomenon is detected by an apparatus comprising a measurement tool for detecting the detectable phenomenon and a computer controller for controlling operation of the measurement tool.

20. The method of claim 19, wherein the at least one biosensor is located in a fixed position on an array comprising a solid support.

21. The method of claim 19, wherein the at least one biosensor is located in a set pattern on a biochip comprising a solid substrate, optionally together with machine readable information encoded on the substrate identifying the location and type of the at least one biosensor.

22. The method of claim 19, wherein the apparatus is portable.

23. A library of biosensors comprising a plurality of biosensors of claim 1 which express different olfactory receptor proteins.

24. An array comprising a solid substrate and at least one biosensor of claim 1 arranged in a fixed position on the substrate.

25. A biochip comprising a solid substrate and at least one biosensor of claim 1 located in a set pattern on said substrate, optionally together with machine readable information encoded on the substrate identifying the location and type of the at least one biosensor on the substrate.

26. A portable container comprising at least one biosensor of claim 1.

27. A method of constructing a biosensor, comprising transfecting one or more yeast to express the following components:
(a) at least one olfactory receptor protein for binding olfactant;
(b) at least one exogenous signaling pathway coupled to the at least one olfactory receptor for transducing a signal produced by the at least one olfactory receptor upon olfactant binding; and
(c) at least one signal reporter coupled to the signaling pathway for producing a detectable phenomenon upon transduction of the olfactant binding signal by the signaling pathway,
wherein the at least one olfactory receptor protein comprises:
(i) an olfactory receptor hypervariable segment which contains at least one olfactant binding site;
(ii) a processing/transport segment which directs the processing and transport of the receptor in the host cell, wherein the processing/transport segment is located N-terminal to the olfactory receptor hypervariable segment; and
(iii) a coupling segment which couples the receptor to the at least one exogenous signaling pathway in the host cell, wherein the coupling segment is located C-terminal to the olfactory receptor hypervariable segment.

28. The method of claim 27, wherein the processing/transport segment comprises the first 60 amino acids of the yeast mam2 protein, and the coupling segment comprises the last 35 amino acids of the rat RI7 receptor.

29. The method of claim 27, wherein the processing/transport segment comprises the first 61 amino acids of the rat RI7 olfactory receptor, and the coupling segment comprises the last 35 amino acids of the rat RI7 receptor.

30. The method of claim 27, wherein the at least one exogenous signaling pathway comprises a G-protein and an adenylate cyclase.

31. The method of claim 27, wherein the at least one signal reporter is responsive to intracellular cAMP or $Ca^{++}$ levels.

32. An expression vector comprising nucleic acid sequences encoding an olfactory receptor protein, wherein the olfactory receptor protein comprises a yeast processing/transport segment, which directs the processing and transport of the receptor in yeast, and a mammalian coupling segment which couples the receptor to an exogenous signaling pathway in yeast, further wherein the processing/transport segment is located N-terminal to the olfactory receptor hypervariable segment, and the coupling segment is located C-terminal to the olfactory receptor hypervariable segment.

33. An expression vector library comprising a plurality of expression vectors of claim 32, which comprise different olfactory receptor hypervariable segments.

34. A method of constructing a library of biosensors, comprising transfecting a plurality of pre-biosensors with the expression vector library of claim 33 so that the pre-biosensors express differing olfactory receptors, wherein each pre-biosensors comprises:
  (a) at least one exogenous signaling pathway coupled to an olfactory receptor for transducing a signal produced by the olfactory receptors upon olfactant binding; and
  (b) at least one signal reporter coupled to the signaling pathway for producing a detectable phenomenon upon transduction of the olfactant binding signal by the signaling pathway.

35. An expression vector comprising nucleic acid sequences encoding an olfactory receptor protein, wherein the olfactory receptor protein comprises a processing/transport segment which directs the processing and transport of the receptor in yeast, and a coupling segment which couples the receptor to an exogenous signaling pathway in yeast, further wherein the processing/transport segment is located N-terminal to the olfactory receptor hypervariable segment, and the coupling segment is located C-terminal to the olfactory receptor hypervariable segment, further wherein the processing/transport segment comprises the first 61 amino acids of the rat RI7 olfactory receptor, and the coupling segment comprises the last 35 amino acids of the rat RI7 receptor.

36. The expression vector of claim 35, wherein the vector is pESCleu-RI7-DH5α.

37. An olfactory receptor protein comprising an olfactory receptor hypervariable segment, a yeast processing/transport segment, which directs the processing and transport of the receptor in yeast, and a mammalian coupling segment which couples the receptor to an exogenous signaling pathway in yeast, wherein the processing/transport segment is located N-terminal to the olfactory receptor hypervariable segment, and the coupling segment is located C-terminal to the olfactory receptor hypervariable segment.

38. A kit comprising:
  (1) one or more pre-biosensors transfected with at least one exogenous cell signaling pathway; and
  (2) one or more vectors adapted to receive an olfactory receptor hypervariable segment, said one or more vectors comprising a cloning cassette and nucleic acid sequences encoding an N-terminal segment and a C-terminal segment of an olfactory receptor, wherein the N-terminal segment directs the processing and transport of the receptor in yeast, and the C-terminal segment couples the receptor to an exogenous signaling pathway, wherein the vectors further comprise nucleic acid sequences encoding an olfactory receptor protein hypervariable segment; wherein said pre-biosensor is yeast.

* * * * *

UNITED STATES PATENT AND TRADEMARK OFFICE
CERTIFICATE OF CORRECTION

| | | |
|---|---|---|
| PATENT NO. | : 7,223,550 B2 | Page 1 of 1 |
| APPLICATION NO. | : 10/467223 | |
| DATED | : May 29, 2007 | |
| INVENTOR(S) | : Natarajan Dhanasekaran and John R. Jenkins | |

It is certified that error appears in the above-identified patent and that said Letters Patent is hereby corrected as shown below:

Title page, Item (54), change "DEFECTING" to -- DETECTING --

In column 1, line 1, change "DEFECTING" to -- DETECTING --

Signed and Sealed this

Fourth Day of March, 2008

JON W. DUDAS
*Director of the United States Patent and Trademark Office*